(12) United States Patent
Jarrett et al.

(10) Patent No.: US 10,617,563 B2
(45) Date of Patent: Apr. 14, 2020

(54) COATED IMPLANTS

(71) Applicant: Incept, LLC, Lexington, MA (US)

(72) Inventors: Peter Jarrett, Lexington, MA (US); Amarpreet S. Sawhney, Lexington, MA (US); Michael J. McGrath, Upton, MA (US); Arthur Driscoll, Reading, MA (US); Ankita D. Desai, Reading, MA (US); Michael Bassett, Pepperell, MA (US)

(73) Assignee: Incept, LLC, Lexington, MA (US)

( * ) Notice: Subject to any disclaimer, the term of this patent is extended or adjusted under 35 U.S.C. 154(b) by 0 days.

(21) Appl. No.: 15/217,559

(22) Filed: Jul. 22, 2016

(65) Prior Publication Data

US 2017/0020729 A1    Jan. 26, 2017

Related U.S. Application Data

(60) Provisional application No. 62/195,580, filed on Jul. 22, 2015.

(51) Int. Cl.
*A61F 9/007* (2006.01)
*A61K 9/00* (2006.01)
(Continued)

(52) U.S. Cl.
CPC ........ *A61F 9/00772* (2013.01); *A61F 9/0017* (2013.01); *A61K 9/0051* (2013.01); *A61K 45/06* (2013.01); *A61K 47/10* (2013.01); *A61L 31/10* (2013.01); *A61L 31/148* (2013.01); *A61L 31/16* (2013.01); *A61L 31/18* (2013.01);
(Continued)

(58) Field of Classification Search
CPC ..................................................... A61F 9/0017
See application file for complete search history.

(56) References Cited

U.S. PATENT DOCUMENTS

| 3,949,750 A | 4/1976 | Freeman |
| 5,283,063 A | 2/1994 | Freeman |

(Continued)

FOREIGN PATENT DOCUMENTS

| CN | 101711708 A | 5/2010 |
| CN | 102176882 A | 9/2011 |

(Continued)

OTHER PUBLICATIONS

VWR (PEG Mw 100,000). Retreieved Apr. 2018.*
(Continued)

*Primary Examiner* — Adam C Milligan
*Assistant Examiner* — Sarah Alawadi
(74) *Attorney, Agent, or Firm* — Christensen Fonder Dardi; Curtis B. Herbert

(57) ABSTRACT

A prosthesis comprising a water-dissolvable coating. A prosthesis for a lacrimal canaliculus comprising a swellable punctal plug with a proximal end and a distal end, with the plug comprising a water-dissolvable biocompatible coating on the distal and/or the proximal end. Materials and methods for making and using the same. A prosthesis for placement in or across natural or prosthetic lumens, ostia, ducts, sinus, or sphincters, the prosthesis comprising a coating. The prosthesis can further provide a depot for sustained drug delivery to tissue.

15 Claims, 12 Drawing Sheets

(51) Int. Cl.
　　　*B29C 35/08*　　(2006.01)
　　　*A61K 45/06*　　(2006.01)
　　　*B29C 41/14*　　(2006.01)
　　　*A61F 9/00*　　(2006.01)
　　　*A61K 47/10*　　(2017.01)
　　　*A61L 31/10*　　(2006.01)
　　　*A61L 31/14*　　(2006.01)
　　　*A61L 31/18*　　(2006.01)
　　　*A61L 31/16*　　(2006.01)

(52) U.S. Cl.
　　　CPC .......... *B29C 35/0805* (2013.01); *B29C 41/14* (2013.01); *B29C 2035/085* (2013.01); *B29K 2023/06* (2013.01)

(56) References Cited

U.S. PATENT DOCUMENTS

| | | |
|---|---|---|
| 5,334,137 A | 8/1994 | Freeman |
| 5,410,016 A | 4/1995 | Hubbell et al. |
| 5,510,418 A | 4/1996 | Rhee et al. |
| 5,514,379 A | 5/1996 | Weissleder et al. |
| 5,874,500 A | 2/1999 | Rhee et al. |
| 6,083,524 A | 7/2000 | Sawhney et al. |
| 6,121,341 A | 9/2000 | Sawhney et al. |
| 6,152,943 A | 11/2000 | Sawhney |
| 6,165,201 A | 12/2000 | Sawhney et al. |
| 6,179,862 B1 | 1/2001 | Sawhney |
| 6,196,993 B1 | 3/2001 | Cohan |
| 6,322,593 B1 | 11/2001 | Pathak et al. |
| 6,379,373 B1 | 4/2002 | Sawhney et al. |
| 6,387,977 B1 | 5/2002 | Sawhney et al. |
| 6,566,406 B1 | 5/2003 | Pathak et al. |
| 6,605,294 B2 | 8/2003 | Sawhney et al. |
| 6,635,457 B1 | 10/2003 | Sawhney |
| 6,673,093 B1 | 1/2004 | Sawhney |
| 6,689,148 B2 | 2/2004 | Sawhney et al. |
| 6,703,047 B2 | 3/2004 | Sawhney et al. |
| 6,818,018 B1 | 11/2004 | Sawhney |
| 6,887,974 B2 | 5/2005 | Pathak |
| 7,009,034 B2 | 3/2006 | Pathak et al. |
| 7,025,990 B2 | 4/2006 | Sawhney |
| 7,211,651 B2 | 5/2007 | Pathak |
| 7,220,270 B2 | 5/2007 | Sawhney et al. |
| RE39,713 E | 7/2007 | Sawhney et al. |
| 7,238,364 B2 | 7/2007 | Sawhney et al. |
| 7,247,314 B2 | 7/2007 | Hnojewyj et al. |
| 7,332,566 B2 | 2/2008 | Pathak et al. |
| 7,413,752 B2 | 8/2008 | Sawhney |
| 7,648,713 B2 | 1/2010 | Sawhney |
| 7,998,497 B2 | 8/2011 | de Juan, Jr. et al. |
| 8,409,606 B2 | 4/2013 | Sawhney et al. |
| 8,563,027 B2 | 10/2013 | Jarrett et al. |
| 2003/0108511 A1 | 6/2003 | Sawhney |
| 2004/0009205 A1 | 1/2004 | Sawhney |
| 2004/0086479 A1 | 5/2004 | Grinstaff et al. |
| 2004/0175410 A1 | 9/2004 | Ashton et al. |
| 2005/0197614 A1 | 9/2005 | Pritchard et al. |
| 2006/0034930 A1 | 2/2006 | Khosravi et al. |
| 2006/0099238 A1 | 5/2006 | Khosravi et al. |
| 2006/0177481 A1 | 8/2006 | Sawhney |
| 2006/0193899 A1 | 8/2006 | Sawhney |
| 2007/0141116 A1 | 6/2007 | Pinchuk et al. |
| 2007/0160647 A1 | 7/2007 | Pritchard et al. |
| 2007/0231366 A1 | 10/2007 | Sawhney et al. |
| 2007/0282366 A1 | 12/2007 | Khosravi et al. |
| 2008/0045911 A1* | 2/2008 | Borgia ............. A61F 9/0017 604/294 |
| 2008/0124400 A1 | 5/2008 | Liggins et al. |
| 2008/0220047 A1 | 9/2008 | Sawhney et al. |
| 2008/0241223 A1 | 10/2008 | Nivaggioli et al. |
| 2009/0017097 A1 | 1/2009 | Sawhney et al. |
| 2009/0227981 A1 | 9/2009 | Bennett |
| 2009/0240276 A1* | 9/2009 | Ainpour ........ A61B 17/12022 606/192 |
| 2009/0306608 A1* | 12/2009 | Li .................. A61F 9/0017 604/294 |
| 2010/0036488 A1 | 2/2010 | de Juan, Jr. et al. |
| 2010/0209478 A1* | 8/2010 | Sawhney ........ A61F 9/00772 424/427 |
| 2010/0280546 A1 | 11/2010 | Campbell et al. |

FOREIGN PATENT DOCUMENTS

| | | |
|---|---|---|
| WO | 2009035571 | 3/2009 |
| WO | 2009111065 | 9/2009 |
| WO | WO 2010/093873 | * 2/2010 |
| WO | 2010071844 | 6/2010 |

OTHER PUBLICATIONS

ChempRep Inc. Overview of Polyethylene Glycol. Dec. 2013.*
SigmaAldrich (Polyethylene Glycol 12,000). Retrieved Apr. 2019.*
Sigma Aldrich (Polyethylene Glycol 35,000). Retreieved Apr. 2019.*
Hill-West et al., "Prevention of Postoperative Adhesions in the Rat by In Situ Photopolymerization of Bioresorbably Hydrogel Barriers," Obstetrics and Gynecology, 83(1):59-64 (1994).
Sawhney et al., "Bioerodible Hydrogels Based on Photopolymerized Poly(ethylene glycol)-co-poly(α-hydroxy acid) Diacrylate Macromers," Macromolecules, 26:581-587 (1993).
Sawhney et al., "Optimization of Photopolymerized Bioerodible Hydrogel Properties for Adhesion Prevention", Journal of Biomedical Materials Research, 28:831-838 (1994).
Sawhney et al., "Rabbit (Pericardial) Adhesion Study", Efficacy Preclinical Studies brochure.

* cited by examiner

Panel a: First Image, t = 0

Panel b: t = 30

Panel c: t = 45

Panel d: t = 60

Panel e: t = 75

Panel f: t = 90

Panel g: t = 100

COATED IMPLANTS

CROSS REFERENCE TO RELATED PATENT APPLICATIONS

This patent application claims priority to U.S. provisional patent application Ser. No. 62/195,580 Filed Jul. 22, 2015 which is hereby incorporated by reference herein for all purposes.

TECHNICAL FIELD

The technical field relates to prostheses with a lubricious coating, including punctal plugs with at least a partial coating.

BACKGROUND

A punctal plug is a small medical prosthesis that is inserted into the lacrimal (tear) drainage duct (punctum) of an eye to block the duct. Blocking the duct prevents the drainage of liquid from the eye into the duct. They are used for dry eye or to deliver therapeutic agent. Other kinds of prostheses are also known in the medical arts for placement in natural lumens. For example urethral implants for delivery of drugs.

SUMMARY

Small implants such as punctum plugs or lacrimal plugs may be used to treat ocular diseases either by mechanically occluding the lacrimal canal to treat conditions such as dry eye syndrome, or by impregnating the implant with a drug that will then be delivered from the implant to treat any number of conditions. Insertion of these small devices or depots into the lacrimal canal can prove challenging due to difficulties such as alignment of the depot with the punctal opening and sliding the implant into the proper position in the lacrimal canal so as not to protrude through the punctal opening. These difficulties have been observed to be compounded when using implants that may swell and/or lose their rigidity upon contact with liquid such as the tear film.

Embodiments of the invention described herein include certain embodiments for application of a dissolvable material to a tip of such an implant to facilitate insertion of the implant. The dissolvable material may be shaped to facilitate alignment with the punctal opening. The material may provide lubrication as it dissolves to reduce the force required for insertion. It may also delay the effects of swelling or softening, in implants that experience this phenomenon, due to contact with the tear film or other liquids.

More generally, other kinds of prostheses can advantageously be treated with dissolvable coatings to facilitate placement. Urethral implants for delivery of drugs to treat erectile dysfunction or other pathologies, for example, are inserted into a urethra. Coatings that lubricate and ease this placement provide improved comfort and improved control over placement. Other prostheses are contemplated for natural or artificial lumens. Natural lumens are openings that occur in the body, and include pathological conditions and normotypical lumens, the latter term meaning that lumens that are normally found in a body in the absence of abnormalities. Some lumens are accessible from outside the body without puncturing a tissue, e.g., an ear canal. Placement of prostheses in other lumens would normally require puncturing a tissue for access, e.g., a cerebrospinal canal.

DETAILED DESCRIPTION

Figure 1A:
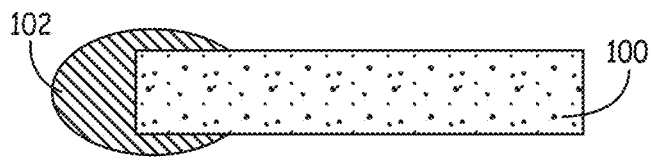
FIG. 1A-1F depicts a prosthesis with coatings on various portions of the prosthesis.
Figure 1B:
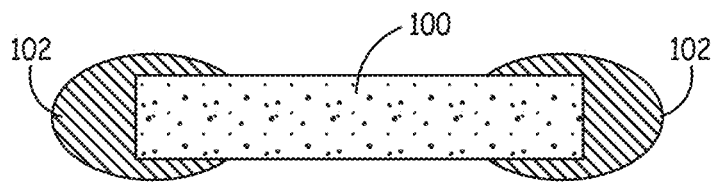
Figure 1C:
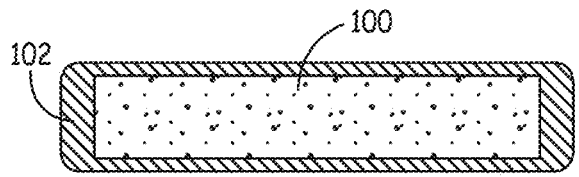
Figure 1D:
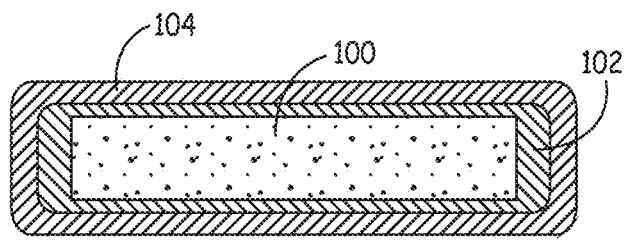
Figure 1E:
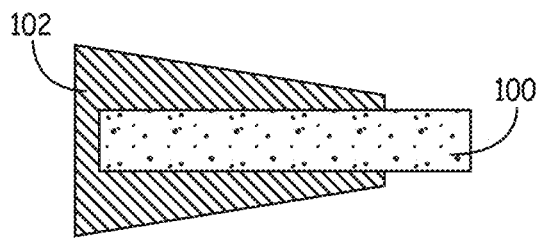
Figure 1F:
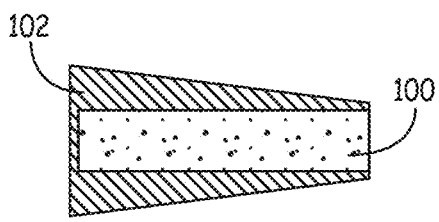

Materials and methods are presented herein that relate to a prosthesis for placement in a lacrimal canaliculus comprising a punctal plug with a coating. The coating delays the entry of water into the plug. An embodiment is a water swellable plug, with the coating being dissolvable in water. Swellable punctal plugs advantageously swell in place in a canaliculus of an eye so that, if they are not overly swollen, the swelling helps to provide a stable seating of the plug, securing it within the canaliculus. It can be useful to coat a portion of such a plug to reduce a rate of entry of fluid into that portion of the plug, so that swelling at that portion is delayed. The term prosthesis is used broadly herein and includes devices that contact a tissue of a patient during their intended use, blood-contacting devices, devices that serve as an artificial body part, drug delivery depots, drug delivery devices, medical devices, catheters, ex vivo medical devices, devices fully implanted within a patient (full implant), and devices that are used in a location that is both exterior and interior to the body (semi-implant). Prostheses may be degradable, non-degradable, temporary, permanent, or an operable combination of the same. A punctal plug is useful for delivery of therapeutic agents to an eye, as described is U.S. Pat. No. 8,409,606; the prostheses described herein, including punctal plugs, may also be used for delivery of therapeutic agents.

Prostheses also include devices that pass into, though, or across natural or prosthetic ostia, lumens, ducts, sinus, or sphincters. A sphincter or other openings create a restricted entry area but a coating on the inserted tip or more generally on the prosthesis facilitates entry without overly dilating the restricted entry area, e.g., sphincter, duct, ostium, lumen, or sinus. Punctal plugs are used as examples herein; prostheses for these other restricted areas are also contemplated. The prosthesis may have any of a variety of shapes: cylindrical, conical, spherical, oblong, or be used on medical devices or medical implants, e.g., catheters, probes, needles, blunt needles, applicators, medical sheaths or dilators, vascular access sheaths or introducers, biopsy devices, rods, tubes, medical tampons.

FIG. 1 depicts punctal plug with coatings on various portions of the prosthesis, e.g., a plug. The prosthesis 100 is depicted with a coating 102 on one of two ends in FIG. 1A, on two of two ends in FIG. 1B, as encapsulating the prosthesis in FIG. 1C or 1D, as coating only one end and part of a portion of the prosthesis between the ends in FIG. 1E, or as coating all but one end in FIG. 1F. The coating is depicted as having various thicknesses, from thin to having a volume comparable to the volume of the plug itself. FIG. 1D depicts a plurality of coatings, with either the outer coating 104 being dissolvable in water or both the outer coating 104 and an inner coating 102 being dissolvable in water. Punctal plugs have a proximal end that is closest to the eye during use, and a distal end that is most distant from the eye during use. Some plugs are symmetrical, with two ends that can each serve as a proximal or a distal end. In general, plugs are asymmetrical, with a distal end that is designed to pass more easily through a puncta relative to the proximal end. In use, the plug is introduced by placing the distal end into the punctum. Some plugs have a proximal end that is enlarged so it does not pass through the punctum. Other plugs are designed to pass entirely through the punctum, into the canaliculus.

Figure 2:
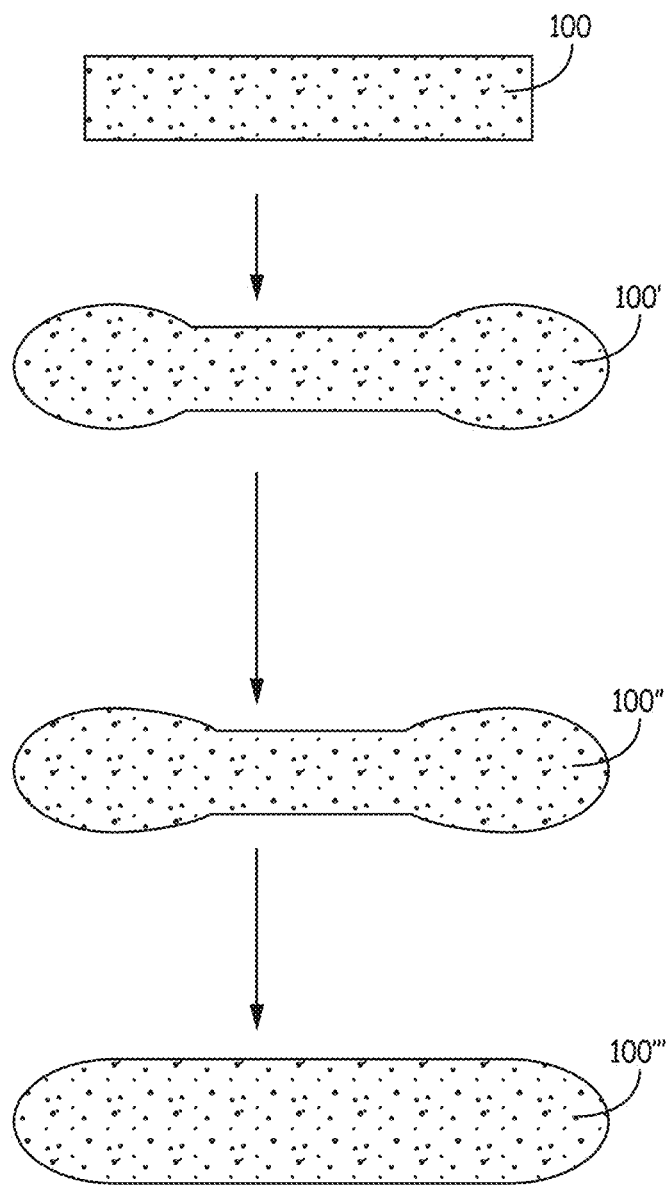
FIG. 2 depicts a prosthesis with ends that swell before a central portion of the prosthesis swells.

FIG. 2 depicts a prosthesis 100, e.g., a punctal plug with ends that swell prior to a central portion. The prosthesis, as a result of a choice of materials, a manufacturing process, use of membranes or impermeable materials or other coatings (not shown) on a portion of the prosthesis, have ends that swell before the other parts of the prosthesis. As depicted, the prosthesis 100 assumes a dumbbell shape 100' in water, with the ends swelling relative to the middle. As time passes, the prosthesis that is being depicted assumes a generally uniform shape 100'', 100''' when not being restrained. In vivo, the tissues around the prosthesis may constrain the swelling and limit a volume of the prosthesis. Some prostheses may be treated with barrier materials that block or reduce a movement of fluids into the plug and/or agents out of the prosthesis.

Figure 3:
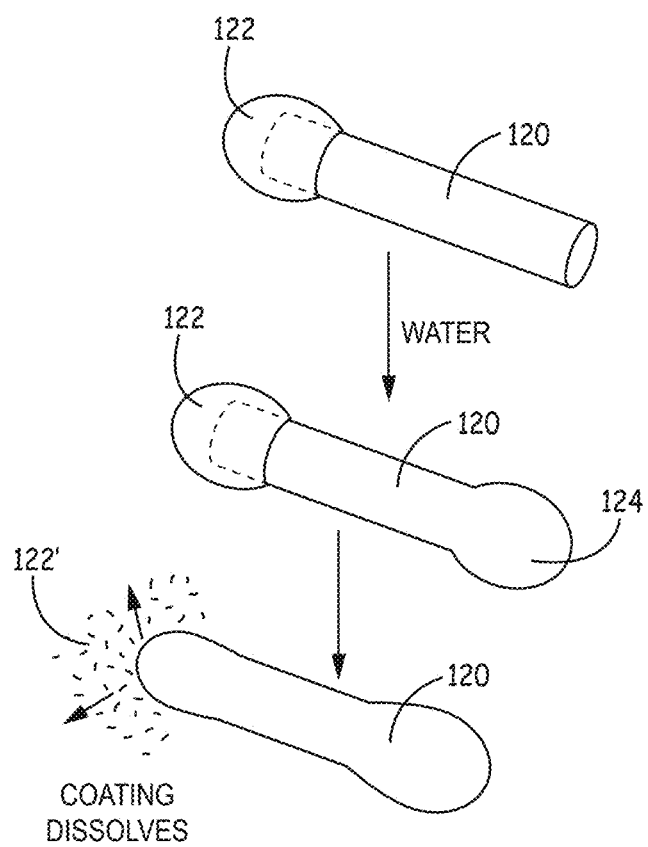
FIG. 3 depicts a prosthesis with a coating on one end, with the coated end swelling slowly in water relative to an uncoated end, and the coating dissolving.
Figure 4A:
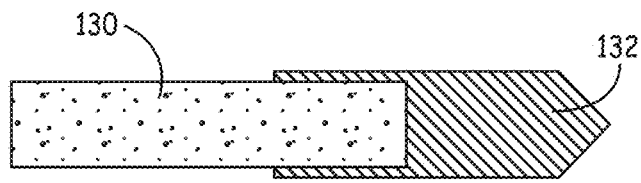
FIGS. 4A-4F depict a prosthesis with a coating formed into a particular shapes.
Figure 4B:
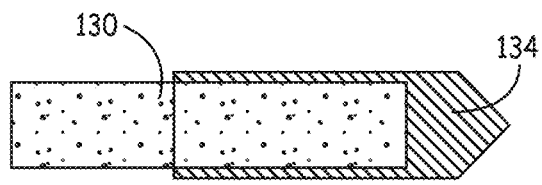
Figure 4C:
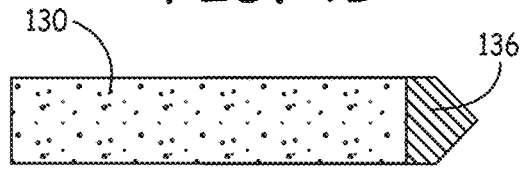
Figure 4D:
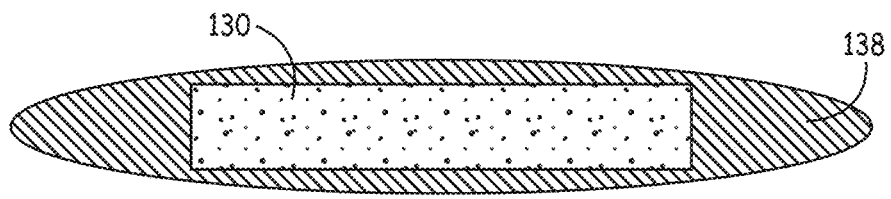
Figure 4E:
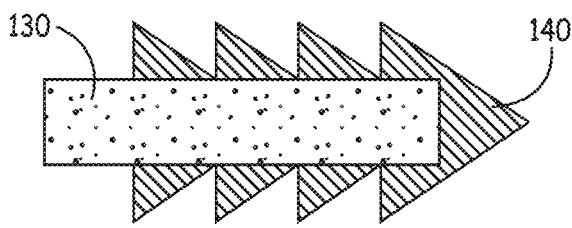
Figure 4F:
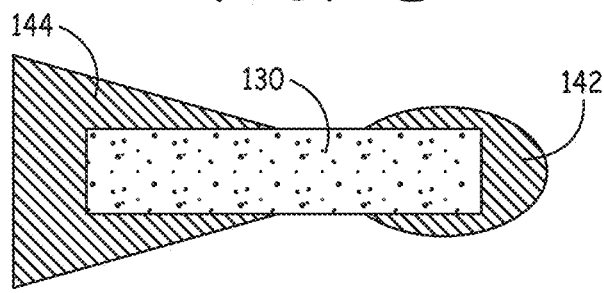
Figure 5A:
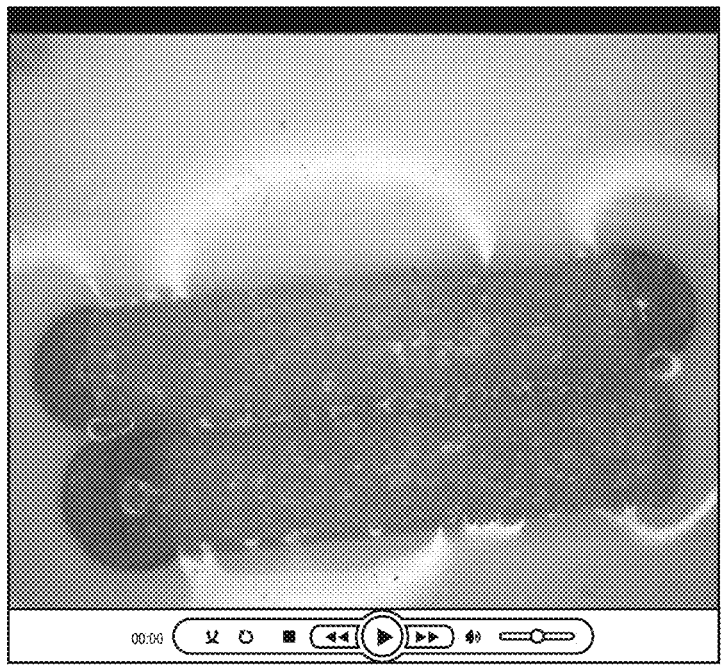
FIG. 5A-5D is a series of time-lapse images of a punctal plug swelling in water, with the plug being coated at one or both ends.
Figure 5A:
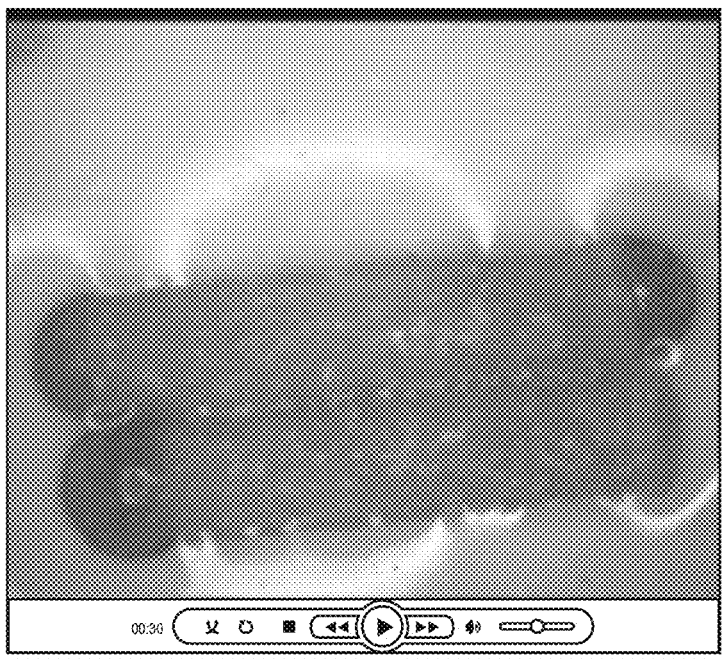
Figure 5B:
Figure 5B:
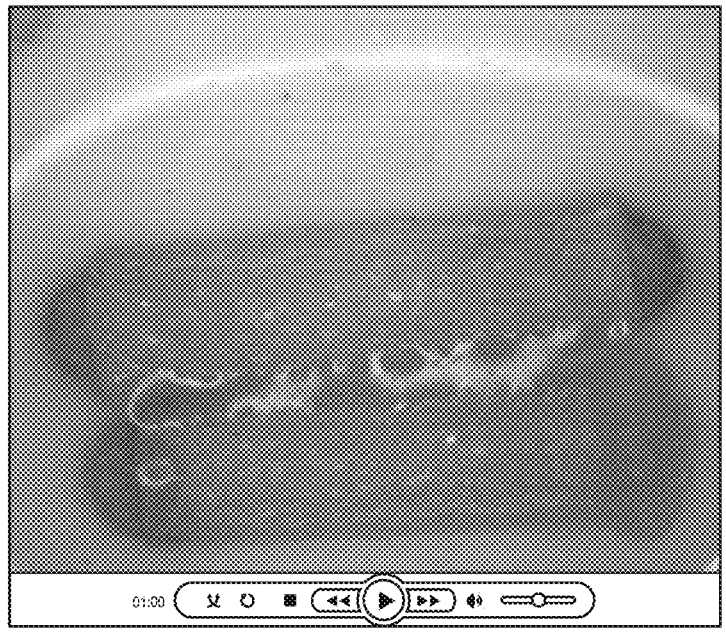
Figure 5C:
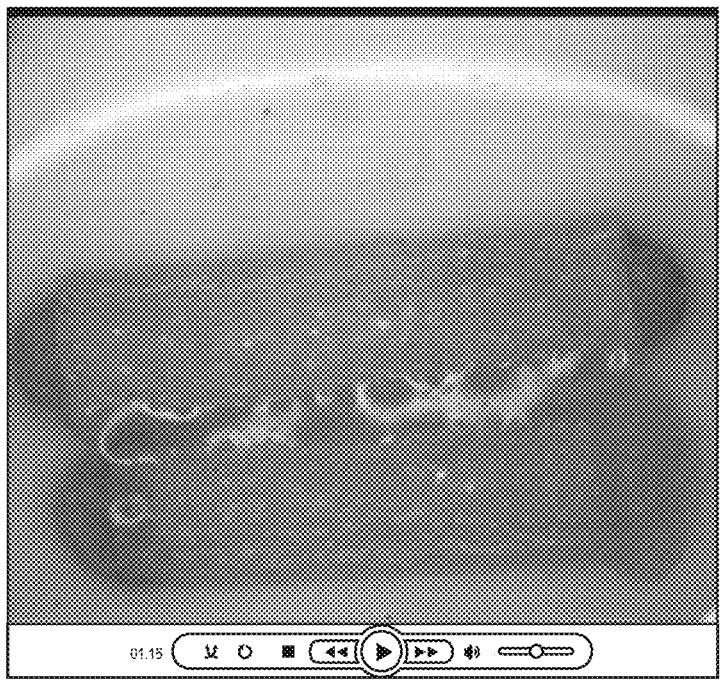
Figure 5C:
Figure 5D:
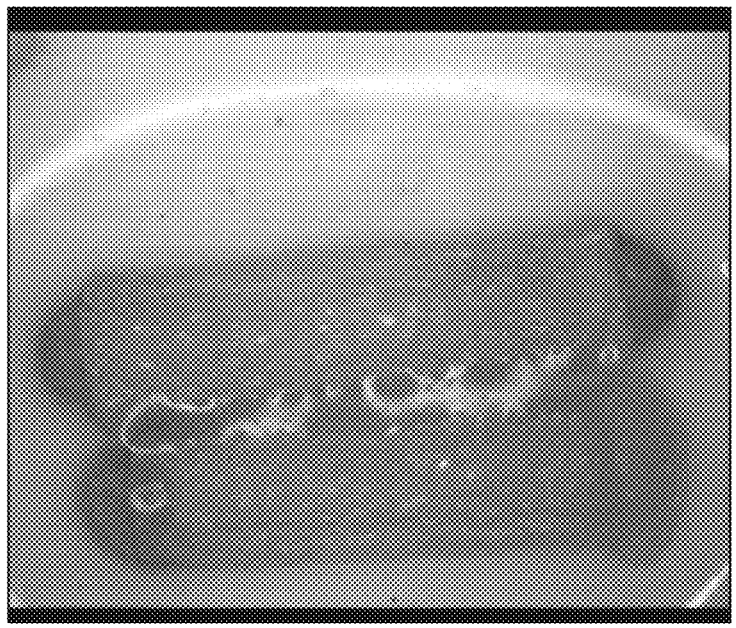

FIG. 3 depicts a swellable prosthesis 120, e.g., a plug with a coating 122 covering one end. The coating may be on a proximal and/or distal end. In water, or aqueous solution, e.g., a physiological solution, prosthesis 120 begins swelling at uncoated end 124. Coated end 122 has little or no swelling. The coating dissolves 122' over time in aqueous solution.

FIG. 4 depicts punctal plugs 130 with coatings 132, 134, 136, 138, 140, 142, 144 that have been shaped. Shapes include features such as points, tapers, rounded-tapers, barbs, collarettes, and rounded ridges.

Figure 6A:
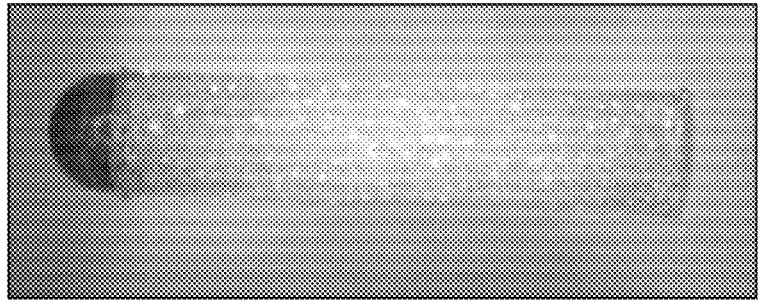
FIG. 6A is a photograph of a punctum plug with a hydrophilic polymer coating at one end.
Figure 6B:
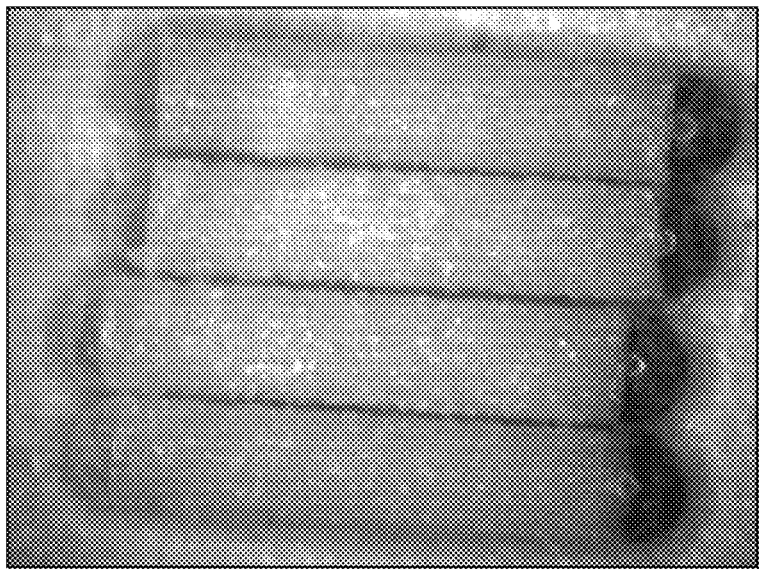
FIG. 6B is a photograph of four of the plugs of FIG. 6A in aqueous solution, with the uncoated ends exhibiting swelling.
Figure 7:
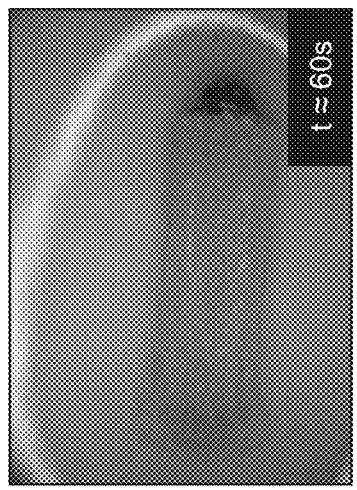
FIG. 7 is a series of time lapse images of a punctum plug in aqueous solution with one coated end swelling slowly relative to an uncoated end.
Figure 7:
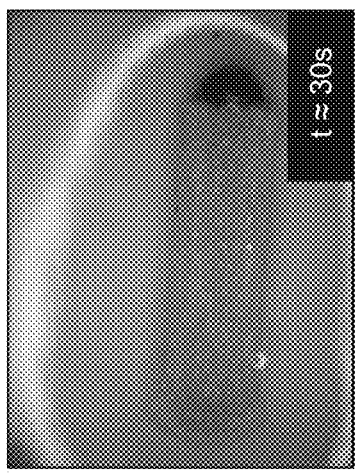
Figure 7:
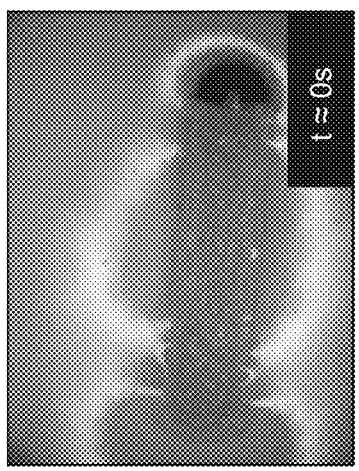
Figure 8:
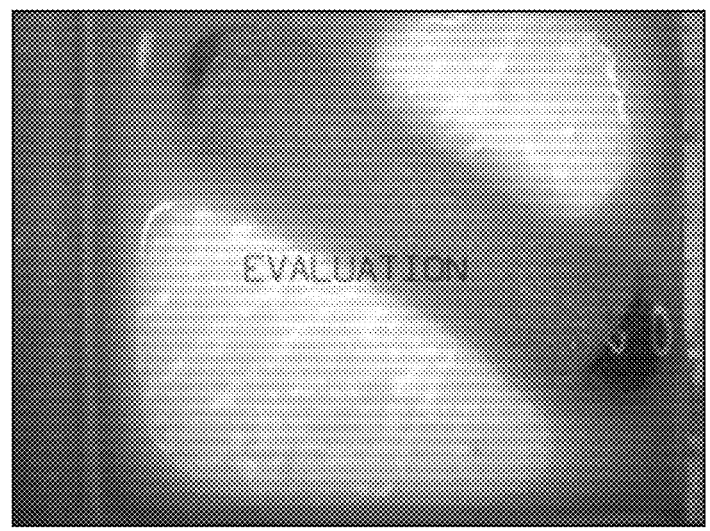
FIG. 8 is a photograph of a punctum plug that has been coated at both ends and allowed to swell for thirty seconds in aqueous solution.
Figure 9:
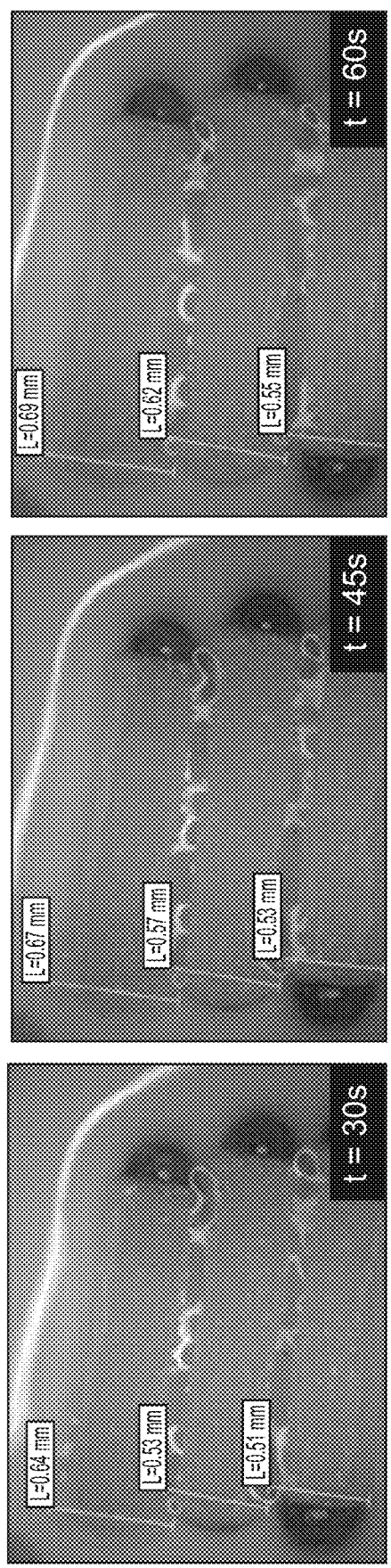
FIG. 9 is a series of photographs showing punctal plugs coated at a proximal and/or distal end, after 30, 45, or 60 seconds in aqueous solution.

FIG. 5 is a series of time-lapse images of a punctal plug swelling in water, with the plug being coated at one or both ends. The rounded, darkened portion at the end is the coating. The plug's starting dimension is 3.2 mm long and 0.72 mm diameter. A dye is present in the coating for visualization. One punctal plug is coated at both ends and the other is coated at only one end. The coating is PEG with a molecular weight of 8000. The plugs have been placed into a physiological solution. The first image depicts the plugs shortly after being immersed (t=0). At 30 seconds, the uncoated end, at its tip, is noticeably swollen. At 45 seconds, the uncoated end is swollen to a mushroom-shape and the nearby portion is visibly large in diameter relative to the other end. The coatings on the dual-coated plug are visibly smaller relative to the ends that they coat. These trends continue at 60, 75, 90, and 100 seconds. FIGS. 6A and 6B are photographs of punctum plugs with a hydrophilic polymer coating at one end. The uncoated ends exhibit swelling. FIG. 7 is time lapse photograph series of a punctum plug with a coating at one end. FIG. 8 is a photograph of a punctum plug that has been coated at both ends and allowed to swell for thirty seconds in aqueous solution; and FIG. 9 is a series of photographs showing punctal plugs coated at a proximal and/or distal end, after 30, 45, or 60 seconds in aqueous solution.

The plug swells rapidly in aqueous solution and the coating slows swelling at the end where it is located. The visualization agent in the prostheses' coating can be used as a guide to a user as to which end to insert into the lumen, with the coating signaling the end that should be inserted first or, alternatively, the coating signaling the end that would be inserted last.

A dissolvable coating may be placed on a prosthesis can be swellable or non-swellable in aqueous solution. The coating may be on all or a portion of the prosthesis. It can be advantageous to coat an entire prosthesis in some instances, either for ease of manufacturing or for use. In the case of some implants, for instance, it can be advantageous to simply coat the entire device since it is small and a large portion of the device is likely to contact sensitive tissue of the user, e.g., a urethral implant. Or a portion of an implant may be left uncoated to enhance water uptake through that portion. It can also be advantageous to have a device that swells preferentially in time, with the coated portion swelling more slowly relative to an uncoated portion. For instance, a device for blocking a cervix can swell preferentially on the distal (innermost) end so that it tends to be secured in place and not pushed out.

The material for the prosthesis itself is limited only by the requirements of its use. The material may be natural or synthetic, a plastic, an engineering plastic, a fluoropolymer, a polyurethane, a hydrogel, a gel, and so forth. The coating can be cohesive with itself so that it tends to resist shearing or displacement. The coating may also be disposed on the prosthesis so that it does not come off in response to shear forces customarily encountered in use, regardless of whether it is adhesive to the prosthesis or not. For instance, a durable coating on a urethral implant can remain cohesive and not be displaced during placement by encapsulation of the implant, even if the coating is not particularly adhesive to the implant.

Materials for a Coating

The coatings may be made with natural and/or synthetic materials, e.g., polymers. Natural materials are those found in nature, including polymers found in nature, and derivatives of the same. Natural polymers include glycosaminoglycans, for example dermatan sulfate, hyaluronic acid, chondroitin sulfates, chitin, heparin, keratan sulfate, keratosulfate, and derivatives thereof. In general, the glycosaminoglycans are extracted from a natural source and purified and derivatized. This modification may be accomplished by various well-known techniques, such as by conjugation or replacement of ionizable or hydrogen bondable functional groups such as carboxyl and/or hydroxyl or amine groups with other more hydrophobic groups. For example, carboxyl groups on hyaluronic acid may be esterified by alcohols to decrease the solubility of the hyaluronic acid. Such processes are used by various manufacturers of hyaluronic acid products to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum.

Natural materials include proteins and peptides. Peptide is a term used herein to refer to a chain of amino acids having no more than 10 residues. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Natural materials include fats, oils, and surfactants. Lipids are a group of naturally occurring molecules that include, e.g., fats, waxes, sterols, fat-soluble viatmins, monoglycerides, diglycerides, triglycerides, and phospholipids. Categories of lipids include fatty acids glycerolipids, glycerophospholipids, sphingolipids, sterol lipids, prenol lipids, saccharolipids, and polyketides.

An advantage of a natural material is that it tends to be available from a cost effective source and has known biological properties. A disadvantage of such materials is that they can be allergenic or immunogenic. Accordingly, coatings may be made that are free of, or essentially free of, amino acids, peptides, proteins, natural materials or any combination of the same. Or the coatings may be free of, or essentially free of, allergenic and/or immunogenic materials, (both natural and synthetic materials). Essentially, in this context, means that there is not enough natural material present to be a concern for provoking discomfort in the patient as an allergen/immunogen, e.g., no more than 1 to 10%; Artisans will immediately appreciate that all ranges and values between the explicitly stated bounds are contemplated, with any of the following being available as an upper or lower limit: 1, 2, 3, 4, 5, 6, 7, 8, 9, or 10 percent.

Synthetic materials may be used to make the coatings. Synthetic polymers are one such material. A polymer is a molecule composed of repeated subunits. The subunits are commonly referred as a monomeric unit or a mer. The term monomer is typically used to refer to a chemical subunit that is reactable to make a polymer. Polymers of only a few monomeric units are sometimes referred to as oligomers. The term polymer includes the meanings of homopolymer, copolymer, terpolymer, block copolymer, random copolymer, and oligomer. A polymer may include a block. A series of identical monomeric units joined together forms a block. A polymer may have no blocks, or a plurality of blocks. A copolymer is a polymer having at least two different monomeric units. Some copolymers have blocks, while others have random structures, and some copolymers have both blocks and regions of random copolymer bonding. Copolymers may be made from reactive monomers, oligomers, polymers, or other copolymers. Synthetic refers to a molecule not naturally found in a human. Some synthetic materials are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Synthetic polymers include polymers made from, or comprising, for example: poly(ethylene) oxide, polyethylene glycol, polyvinyl pyrrolidinone, polyacrylate, polymethylacrylate, polyalkylene oxide, methacrylic acid or other vinylic monomers, an acyl chloride, for example methacryloyl chloride, an isocyanate, or 2-isocyanatoethyl methacrylate an electrophilic poly(ethylene glycol) methacrylate (PEGMA). Free radical polymerization is, in general, accomplished with a vinylic or allylic group, including acrylates and methacrylates. A monomer may be polymerized by itself or with co-monomers that also undergo free radical polymerization. Examples of co-monomers include one or more of: acrylates, methacrylates, 2-hydroxyethyl methacrylate, hydroxypropyl methacrylate, n-butyl methacrylate, tert-butyl methacrylate, n-hexyl methacrylate, 2-methoxyethyl methacrylate, poly(hexanide) methacrylate, poly(hexanide) polyethylene oxide methacrylate, or alkyl derivatized poly(hexanide) methacrylate, heparin derivatized polyethylene oxide macromer, vinyl sulfonic acid monomer, monomers comprising poly(ethylene glycol), N-vinyl pyrrolidone monomers, 4-benzoylphenyl methacrylate allyl methyl carbonate, allyl alcohol, allyl isocyanate, methacryloyloxyethyl phosphorylcholine, glycerol monomethacrylate, and polymers containing phosphate and amine moieties. Various polymers include, for instance: hydrophilic polymers, hydrophobic polymers, polyalkylene oxides, polyethylene oxide, polyethers, and polyvinylpyrrolidone.

Coatings or Materials that are Hydrophobic, Hydrophilic, or In-Between

The materials, and the coatings, may be hydrophilic, substantially hydrophilic, or hydrophobic. The term hydrophobic means a material that is substantially insoluble in water even if pH and ionic conditions are adjusted, recognizing that even hydrophobic materials theoretically have some very small amount of solubility. A hydrophilic material is one that is made of water soluble materials, even if the hydrophilic material cannot dissolve in water; for instance, a crosslinked hydrogel made of hydrophilic materials does not dissolve. Materials that have hydrophobic portions can dissolve in aqueous solution if they have enough hydrophilic portions to counterbalance the effects of the other portions. Some chemical groups are hydrophilic, such as hydroxyl groups, carbonyl groups, carboxyl groups, primary amino groups, sulfhydryl, phosphate groups, and hydrophilic linkages such as ethers, and unhindered esters. A water soluble material has a solubility of at least 1 g/100 mL in an aqueous solution. A substantially water soluble material is not hydrophobic but does not dissolve at 1 g/100 mL in water. A substantially hydrophilic material is made of substantially hydrophilic materials or a combination of materials that, in the aggregate, for substantial hydrophilicity. Coating materials may be chosen to provide lubricity.

Examples of hydrophilic materials are polyethylene glycol, polyvinyl alcohol, polyvinylpyrrolidone, cellulose, polyacrylic acid, polyethyleneimine, many peptides or proteins, and many of the polysaccharides. Examples of hydrophobic materials are lipids, waxes, alkanes, perfluorinated polymers, polypropylenes, and polyethylenes. Surfactants can fall into either group, or in-between, depending on the mix of chemical groups. Examples of surfactants are polyethylene oxide-polypropylene oxide block copolymer, PLURONICs, PLURONIC F127, POLYSORBATEs, POLYSORBATE 80, TWEENs, TWEEN 40, and TETRONICS.

Dissolving

The coatings may be dissolving coatings, meaning they dissolve in a physiological solution. Dissolving typically takes place by the material of the coating moving from a solid phase into solution. Dissolving is to be distinguished from a coating that loses adherence and sloughs off in water, e.g., a hydrogel that does not dissolve. The coatings may be made of hydrophilic materials, e.g., polyethylene glycol, polyvinyl alcohol, polyvinylpyrrolidone, cellulose, polyacrylic acid, polyethyleneimine, peptides, proteins or polysaccharides. Other materials, mixtures of materials, or poorly soluble particulate filler additives may be used if a lesser rate of dissolution is desirable. Covalently crosslinked materials, e.g., hydrogels, will not be dissolved. Other crosslinks will generally prevent a material from dissolving or slow the rate thereof.

A material or a polymer for a dissolvable coating may have a hydrophobic portion provided that it is nonetheless soluble or substantially soluble in water because it also has a hydrophilic portion some hydrophobic portions may include a plurality of alkyls, polypropylenes, alkyl chains, or other groups. Some polymers with hydrophobic portions are sold under the trade names PLURONIC, JEFFAMINE, or TETRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

A coating that is dissolvable in water may be made with various materials. Water soluble materials or substantially water soluble materials may be used that go into solution in physiological solution. Pores or channels may be present to help accelerate dissolving. For instance, a polymer-powder mixture may be used to make the coating, with the powder being removed in a solvent that does not dissolve the polymer, thereby leaving pores or channels. Effervescent agents may be included to generate forces that help break up the coating so its components may go into solution. A mix of highly water soluble and less water soluble materials may be combined to control a time of dissolution. Insoluble, slowly soluble, or bioabsorbable particulate additives may be used to slow the dissolution rate.

The coating may comprise, or consist essentially of, a polyethylene glycol (PEG, also referred to as polyethylene oxide when occurring in a high molecular weight) refers to a polymer with a repeat group $(CH_2CH_2O)_n$, with n being at least 3. Essentially, in this context for a PEG that is not crosslinked, means that other materials that are present do not contribute meaningfully to a rate of dissolution of the coating, i.e., have no more than a 10% speed/slow of the dissolution rate. If the PEG is crosslinked, then essentially means that the coating has no more than 5% w/w of other materials, bearing in mind that a crosslinked PEG forms an insoluble hydrogel. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. For instance, 8a15 KPEG is an 8-armed PEG of about 15,000 MW. PEGs of more than about 3000 MW are highly water soluble.

A choice of materials, dissolution aids, thickness, and disposition on the prosthesis, e.g., plug can be made to set a time of dissolving. Embodiments of the invention include coatings that dissolve in less than about 24 hours. Artisans will immediately appreciate that all ranges and values between the explicitly stated bounds are contemplated, with any of the following being available as an upper or lower limit: 10 seconds, 1, 2, 3, 4, 5, 10, 15, 20, 60, 100, or 120 minutes; 1, 2, 3, 4, 5, 6, 12, 16, 18, 20, 22, or 24 hours. Accordingly, e.g., a time in a range from 30 seconds to 5 minutes is contemplated, or less than five minutes.

Biodegradable

The term biodegradable refers to a break-down of materials by in vivo causes, be they enzymatic, cellular, or hydrolytic. Hydrolytic degradation (also referred to herein as water-degradable) can be a subcategory of biodegradable, and refers to degradation of the links in a polymer or other material by water, e.g., breaking of ester bonds. A coating may be formed so that, upon hydration in physiological solution, a material is formed that is water-degradable, as measurable by the material losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

Crosslinking, Blending, and Layers

The coatings may be made of blended materials. The materials are present together without crosslinks between them. Materials for the coatings may be in layers that form zones of distinct materials. Or the coatings may be made from precursors that are crosslinked with each other. Crosslinking generally renders the coatings insoluble, or at least the portions of the coatings wherein the material is crosslinked together. The coatings may be free of crosslinks or essentially free of crosslinks; the term essentially, in this context, means that the material is incompletely crosslinked and will dissolve in an excess of physiological solution at 37° C. within 48 hours or less. Crosslinks can be formed by covalent bonds or physical bonds. Examples of physical bonds are ionic bonds, hydrophobic association of precursor molecule segments, and crystallization of precursor molecule segments. Accordingly, the coatings may be free of both types of crosslinks, or free of covalent crosslinks, or free of physical crosslinks; as is evident, such coatings are free of crosslinks at the time of intended use in aqueous solution and also prior to use, e.g., when stored.

To form covalently crosslinked coatings, the coating materials, e.g., polymers, must be covalently crosslinked together. In general, polymeric precursors are polymers that will be joined to other polymeric precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architectures. In the case of biodegradable coatings, a crosslinked material can be made that will degrade in aqueous solution so that the coating dissolves over time.

In some embodiments, a crosslinked or crosslinkable coating is made with one or more multifunctional precursors, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products. Accordingly, when making coatings that are free of crosslinks, such coatings can be made without functional groups that react with each other and/or without crosslinks that react with tissue, e.g., the polymers or other materials in the coating are free of electrophilic groups that are reactive with nucleophilic groups, are free of unsaturated bonds, are free of nucleophilic groups, are free of functional groups that form covalent bonds with each other, are free of groups that form physical binds with each other and so forth. While carboxyl's, thiols, and amines and certain other functional groups are present in tissues, they are not reactive in the absence of suitable activated functional groups. The hydrogel arts include materials that form hydrogels by physical bonds: although many chemical groups can undergo some theoretical degree of physical bonding with each other, it is customary for artisans to refer to materials as forming physical bonds when they are capable of forming a material that does not dissolve in water. Embodiments include coatings that are free of materials that undergo physical bonding with each other such that the coatings do not form a hydrogel and/or such that the coatings dissolve in water within a certain period of time as set forth elsewhere herein.

The term precursor refers to the polymer, macromer, monomer, functionalized protein, or other component that is a component used to make the coating. The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A precursor may also be a macromolecule (or macromer), which is a molecule having a molecular weight in the range of a thousand to many millions. The coating may be made with at least one of the precursors as a small molecule of about 1000 Da or less (alternatively: 2000 Da or less). The macromolecule, when reacted in combination with a small molecule (of about 1000 Da or less/200 Da or less), is preferably at least five to fifty times greater in molecular weight than the small molecule and is preferably less than about 60,000 Da; artisans will immediately appreciate that all the ranges and values within the explicitly stated ranges are contemplated. Synthetic precursors may be used.

Methods of Application of a Coating

A method of applying the coating comprises dipping the portion of the prosthesis, e.g., a plug, to be coated into a melt of polymer or polymers that form the coating. Polymers that melt at a temperature of no more than about 100° C. are melted in the absence of solvents. The prosthesis, or portion thereof, is dipped into the melt. The melt is allowed to cool to a solid, and remains a solid at 37° C. Instead of dipping the prosthesis into the melt, the melts may be otherwise applied, e.g., brushing, rolling, dropping melt onto the prosthesis, and so forth.

The term melt, in the context of a polymer, refers to a polymer that is in a liquid state but is not dissolved in a solvent, or the polymer acts as its own solvent. Some other materials may be present in the melt, but they are not solvents for the melt. It is recognized that some small amount of a solvent can be present in a concentration that is not effective to dissolve a substantial portion of the polymers in the melt, e.g., no more than 10%, weight per total weight; Artisans will immediately appreciate that all ranges and values between the explicitly stated bounds are contemplated, with any of the following being available as an upper or lower limit: 0.1, 0.2, 0.5, 1, 2, 3, 4, 5, 6, 7, 8, 9, or 10, referring to % weight/total weight. Agents may be present in the melt that assist in adjusting its melting point. For instance, addition of agents that reduce the forces of association between polymers (plasticizers) may be added to reduce a melting point; such agents may be non-solvents or solvent. Such agents may be added at, e.g., no more than 10%, weight per total weight; Artisans will immediately appreciate that all ranges and values between the explicitly stated bounds are contemplated, with any of the following being available as an upper or lower limit: 0.1, 0.2, 0.5, 1, 2, 3, 4, 5, 6, 7, 8, 9, or 10, referring to % weight/total weight. Also, the use of branched polymers may be used to adjust melting temperatures.

An example of polymers that melt at a temperature that is reasonable for dipping the punctal plug or other prosthesis without damaging the prosthesis includes PEGs, with the melting point being related to the MW of the PEG. A PEG of about 8,000 MW has been tested and is useful. Other MWs for PEGs are, for instance, from about 2,000 to about 100,000 (MWs for polymers refer to a weight average molecular weight unless otherwise specified). In general, the polymer or mixture of polymers is chosen to set the desired melt temperature and the target dissolving time.

A method of applying a coating to a prosthesis comprises exposing a prosthesis to a solution comprising the polymer(s) that will form the coating, with the polymer(s) being in solution in a solvent that is not a solvent for the prosthesis. The solvent, in general, is non-aqueous and is an organic solvent. Examples of organic solvents are dimethylcarbonate, dimethylformamide dimethyl sulfoxide, n-methyl pyrrolidinone, dimethyl sulfoxide, ethyl lactate, N-dicyclohexylcarbodiimide, methylene chloride, chloroform, and acetone. Other solvents that may be used are alcohols: ethanol, isopropanol, 1, 2-propane diol, 1,4-butane diol.

The coatings may be made using water to dissolve coating materials to make a solution that is sprayed onto a prosthesis to make a water soluble coating, a process referred to as a fluidized bed. An alternative configuration could use a coating material that dissolves in a non-aqueous solvent to form a non-aqueous solution. Coatings may also be applied by brushing, dipping, or customary coating processes.

Pores or channels may be present to help accelerate dissolving. For instance, a polymer-powder mixture may be used to make the coating, with the powder being removed with a solvent that does not dissolve the polymer, thereby leaving pores or channels.

A coating on an end may be made with an amount of material that is from 1% to 20% of the total weight of the prosthesis; Artisans will immediately appreciate that all ranges and values between the explicitly stated bounds are contemplated, with any of the following being available as an upper or lower limit: 0.1, 0.5, 1, 2, 3, 4, 5, 6, 7, 8, 9, 10, 12, 14, 15, 16, 17, 18, or 20. In terms of total coating volume for one end, either end, or total of all coating, a volume from 0.1 to 5000 microliter may be useful, Artisans will immediately appreciate that all ranges and values between the explicitly stated bounds are contemplated, with any of the following being available as an upper or lower limit: 0.1, 0.5, 1, 2, 5, 10, 15, 20, 25, 50, 100, 150, 200, 250, 500, 750, 900, 1000, 2000, 3000, 4000, 5000 microliters. The coating volume can be chosen in light of the prosthesis size, or other implant's size, and the intended use.

For a typical tip that enters the punctum, the tip length is about 0.2-0.5 mm long and has a diameter similar to but not greater than the plug (0.7 mm approx.), and may have a tapered tip. The coating advantageously has enough material to provide lubricity as a plug enters punctum and transfers lubricity along length of plug as it passes along canaliculus. An excessive quantity of material which may increase the plug's diameter or overly increase its length, which may be detrimental to ease of insertion. Plugs, or other prostheses may range from, e.g., 0.01-5 mm; Artisans will immediately appreciate that all ranges and values between the explicitly stated bounds are contemplated, with any of the following being available as an upper or lower limit: 0.01, 0.1, 0.2, 0.3, 0.35, 0.4, 0.5, 0.6, 0.7, 0.8, 1, 2, 3, 4, 5 mm. A plug or other prosthesis diameter may be, e.g., from 0.01 to 3 mm; Artisans will immediately appreciate that all ranges and values between the explicitly stated bounds are contemplated, with any of the following being available as an upper or lower limit: 0.01, 0.05, 0.1, 0.2, 0.3, 0.4, 0.5, 0.6, 0.7, 0.8, 0.9, 1, 2, 3 mm. The tip added to the prosthesis, the tip comprised of the coating, may be, e.g., from 0.01 to 3 mm in length and/or diameter; Artisans will immediately appreciate that all ranges and values between the explicitly stated bounds are contemplated, with any of the following being available as an upper or lower limit, the length and diameter being independently selected from: 0.01, 0.02, 0.03, 0.04, 0.05, 0.1, 0.2, 0.3, 0.4, 0.5, 0.6, 0.7, 0.8, 0.9 1, 2, 2.5, or 3 mm. A tip may be the distal tip or a proximal tip. The tips may be the same size or different sizes. In some cases, it is useful for the proximal tip to be smaller than the distal tip, e.g., about 30% to 80% of its volume; Artisans will immediately appreciate that all ranges and values between the explicitly stated bounds are contemplated, with any of the following being available as an upper or lower limit: 10, 20, 25, 33, 35, 40, 45, 50, 55, 60, 65, 70, 75, 80.

Coatings that are thin on the sides of a prosthesis, e.g., a plug and thick at the proximal and/or distal end are embodiments of the invention. A fast dissolving coating on the sides may be used to provide lubricity along length and to negate the need for a bolus of material at the distal tip. The coating is thick at the ends to retard end swelling. For example a coating could be from 0.001 to 0.3 mm thick on sides and from 2× to 20× that on the ends; Artisans will immediately appreciate that all ranges and values between the explicitly stated bounds are contemplated, with any of the following being available as an upper or lower limit: 0.001, 0.002, 0.003, 0.004, 0.005, 0.006, 0.007, 0.008, 0.009, 0.01, 0.02, 0.03, 0.05, 0.07, 0.09, 0.1, 0.15, 0.2, 0.25, 0.03 mm and that the ends may be independently chosen to be, relative to the chosen thickness, 2, 2.5, 3, 3.5, 4, 5, 6, 7, 8, 9, or 10× thicker.

Coatings may be applied to all or a portion of a prosthesis, e.g., a plug, implant, and so forth. In some embodiments, two or more coatings are applied to all or a portion of a prosthesis, e.g., different coatings contact different ends, one covers the other. For example, a prosthesis, e.g., a punctum plug may have a first coating that contacts a proximal or distal end and a second coating that contacts the other end, i.e., a distal or proximal end. The first coating and/or second coating may comprise a visualization agent and the first and/or second coating may have the same or different visualization agents. The first and/or second coating may be made of the same materials or different materials. One embodiment is the prosthesis with a visualization agent in the first coating and no visualization agent in the second coating. Another embodiment is a first visualization agent in the first coating and a second visualization agent in the second coating. An embodiment is a punctal plug with a coating on the proximal end that has a visualization and a coating on the distal end with no visualization agent. These combinations can provide various advantages, e.g., a color-code to indicate which end enters into the punctum or other tissue first, a color-code to indicate position, e.g., left eye or right eye, a color code to indicate contents, e.g., a presence or type of therapeutic agent, a code for degradability, e.g., a first color indicates degradation over a first period of time and a second color (or absence of color) indicates degradation over a second period of time. Color coding according to coating can also be used, e.g., to indicate a size, with a first color indicating a first size, a second color indicating a second size, a third color indicating a third size, and so forth. These combinations can advantageously be used to provide different coatings on different portions of a prosthesis, with the coating contents being optionally color coded. For instance, the first coating may be shaped into a point (may comprise an internal angle taken through the coating of 90 degrees or less) for ease of insertion and the back end shaped as a flat or rounded surface (blunt surface) to accommodate a pusher. Or the first coating may be designed to dissolve in a first period of time and the second coating to dissolve in a second period of time (please refer to examples of periods of time provided elsewhere herein).

Accordingly, embodiments include a prosthesis for placement in a lumen, the prosthesis comprising a coating on a portion of the prosthesis, wherein the coating comprises a visualization agent to indicate an orientation of the prosthesis at its site of intended use. For example, a punctal plug with a colored distal end is thus indicated as being oriented distally when in use.

Sites of Administration

Sites of administration include openings in a tissue. One embodiment is a punctal plug that is placed into a lacrimal canaliculus. Other embodiments are prostheses or implants passed into or through or across a natural or artificial lumen, e.g., a sphincter, duct, ostium, sinus or other lumen. Artificial lumens are made for medical purposes, e.g., to deliver a drug, for surgery, or other medical or cosmetic purposes.

Coatings on the prosthesis can ease passage of the prosthesis through the openings by contacting the tissue around the opening. The prosthesis is sized appropriately. For example, artisans are accustomed to sizing punctal plugs such that the plug is sized to allow the coating to contact the walls of point of entry into the canaliculus.

Natural lumens include nasal cavities, sinus cavities, lacrimal canals, hyaloid canal, ear canals, inner ear, cerebrospinal canal, epidural space, urethra, ureter, a sinus of an organ, a liver sinus, a renal sinus, paranasal sinuses, maxillary sinus, ethmoid sinus, sphenoid sinus, frontal sinus, subcapsular sinus, medullary sinuses, trabecular sinuses, dural venous sinuses, inferior sagittal sinus, superior sagittal sinus, straight sinus, occipital sinus, confluence of sinuses, cavernous sinus, superior petrosal sinus, inferior petrosal sinus, transverse sinus, sigmoid sinus, carotid sinus, renal sinus, a coronary sinus, a fallopian tube, and a seminal vesicle. Further lumens are a Schlemm's canal, or anterior and posterior chambers in an eye.

Ostia for use with the prostheses/coatings include ostium of fallopian tube, ostium of the uterus, ostium primum of the developing heart, ostium secundum (foramen ovale) of the developing heart, ostium maxillare of the maxillary sinus, ostium vaginae (vaginal orifice), coronary ostium (opening of coronary arteries at root of aorta, superior to aortic valve), sinus ostium (an opening that connects a sinus to a nasal cavity ostium of uterine tube), ostium abdominale (the funnel-shaped opening where the uterine tube meets the abdominal cavity), coronary ostium, ostium internum uteri, ostium pharyngeum tubae auditivae (the pharyngeal opening of the auditory tube), tympanic ostium, ostium cardiacum (the opening of the esophagus into the stomach), coronary ostium (either of the two openings in the aortic sinuses which mark the origin of the (left and right) coronary arteries), ostium ejaculatorium (the common orifice of the ductus deferens and the excretory duct of the seminal vesicle into the urethra), ostium internum, ostium pharyngeum (the nasopharyngeal end of the auditory tube), ostium primum (an opening in the lower portion of the membrane dividing the embryonic atria into right and left sides), atrial septal defects, ostium pulmonary vein (the opening of the pulmonary vein into the left atrium), ostium ruminoreticulare (the opening between the rumen and the reticulum), ostium secundum (an opening in the upper portion of the membrane dividing the embryonic atria into right and left sides, appearing later than the ostium primum).

Sphincters for use with the prostheses/coatings include anal sphincter, cardiac sphincter, cardioesophageal sphincter, external sphincter of female urethra, external sphincter of male urethra, gastroesophageal sphincter, hepatic sphincter, internal sphincter of urethra, O'Beirne's sphincter, sphincter of Oddi, pharyngoesophageal sphincter, precapillary sphincter, pyloric sphincter, rectal sphincter, tubal sphincter, vesical sphincter, ilela sphincter, ileocecal sphincter, pupillary sphincter, reticulo-omasal sphincter, teat sphincter, urethral sphincter, and perineal sphincter.

Ducts for use with the prostheses/coatings include lactiferous duct, cystic duct, common hepatic duct, common bile duct, pancreatic duct, parotid duct, submaxillary duct, major sublingual duct, Bartholin's ducts, intralobular duct, interlobular duct, interlobar duct, bile duct, tear duct, ductus deferens, pancreatic duct, liver duct, canalis vertebralis, spinal canal, vertebral canal, ampulla, Haversian canal, epididymis, deminal duct, ejaculatory duct, bronchiole, lactiferous duct, and thoracic duct. Other embodiments are directed to a prosthesis that is coated for purposes of introduction into a tissue, meaning into a target tissue or through a tissue to place an implant in contact with a target tissue. For instance, implants into an eye may be coated for purposes of easing introduction of the implant. Or implants made percutaneously may be coated for easier passage into the body.

Coatings may be applied to implants that target a blood vessel. For instance, implants used to occlude a blood vessel may receive a dissolvable coating as set forth herein. Prostheses as already described may be implanted. Examples include beads, particles, microparticles, hydrogels, and solids.

The prostheses may be used to treat conditions associated with the lumen. For instance, a sinus may be treated with a prosthesis to delivery an anti-allergenic, an anti-inflammatory, an antihistamine if the since is inflamed or reactive to allergies. Erectile dysfunction (ED) may be treated with ED agents delivered from a prosthesis in the male ureter. Contraceptives may be delivered from a prosthesis placed in a fallopian tube or seminal vesicle.

Therapeutic Agents

The prostheses and/or coatings may comprise a therapeutic agent. The agent may be for a medical use, e.g., to treat a medical condition, to treat a disease, to provide comfort for a patient, pain control, cosmesis, or other purposes. Conventional processes for placing an agent in the prosthesis or coating may be used. Agents may be introduced at the time of making the prosthesis or coating or afterwards. Agents may also be for use in radiation therapies or medical imaging. For instance, radioactive implants, radiotherapy agents, brachytherapy implants, toxins, anticancer agents. And for instance, imaging agents for radiology.

Therapeutic agents include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., anti-VEGF, blocks VEGFR1, blocks VEGFR2, blocks VEGFR3, anti-PDGF, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRES SA), toceranib (PALLADIA), Erlotinib (TARCEVA), Lapatinib (TYKERB) Nilotinib, Bosutinib Neratinib, lapatinib, Vatalanib, dasatinib, erlotinib, gefitinib, imatinib, lapatinib, lestaurtinib, nilotinib, semaxanib, toceranib, vandetanib.

The therapeutic agent may comprise a macromolecule, for example an antibody or antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Eylea™ (aflibercept or VEGF Trap), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of trimacinalone, trimacinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.)

Therapeutic agents may include various classes of drugs. Drugs include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antibiotics, pain relievers, inhibitors of vascular endothelial growth factor (VEGF), chemotherapeutics, antiviral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides of various molecular weights. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, is an antibody that binds VEGF. And AFLIBERCEPT is a fusion protein that includes portions of a VEGF receptor to trap VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Oxifloxacin is the active ingredient in VIGAMOX, which is a fluoroquinolone approved for use to treat or prevent ophthalmic bacterial infections. VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, permeation agents for an eye.

The agent may be treatment of a back of the eye disease, e.g., wherein the back of the eye disease is age-related macular degeneration (AMD) cystoid macular edema (CME), diabetic macular edema (DME), posterior uveitis, and diabetic retinopathy, or glaucoma.

The agents may be, e.g., an agent comprises anti-VEGF, blocks VEGFR1, blocks VEGFR2, blocks VEGFR3, anti-PDGF, anti-PDGF-R blocks PDGFRβ, an anti-angiogenic agent, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinibn gefinitib, toceranib, Erlotinib, Lapatinib, Nilotinib, Bosutinib Neratinib, lapatinib, Vatalanib, comprises low-soluble prostaglandin analogues for glaucoma, nepafenac, macrolides, rapamycin, sirolimus, tacrolimus, or serves to block mTOR receptors for AMD (also known as choroidal neovascularization (CNV). mTOR refers to mammalian target of rapamycin. Agents may be, e.g, moxifloxacin, dexamethasone, travoprost, steroids, fluoroquinolones, prostaglandin analogs, prostamides.

Eye Disease States

The materials described herein may be used to deliver drugs or other therapeutic agents (e.g., imaging agents or markers) to eyes or tissues nearby. Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other ocular conditions may be provided by delivery of agents from a prosthesis, e.g., punctal plug.

Kits or Systems

Kits or systems may be prepared. The kits are manufactured using medically acceptable conditions and contain prostheses that have sterility, purity and preparation that is pharmaceutically acceptable. The kit may contain an applicator as appropriate, as well as instructions. A therapeutic agent may be included. In some embodiments, the kit has at least one prosthesis and an applicator. Or a kit may comprise a plurality of prostheses, e.g., of varying sizes, various coatings, various agents, or a combination thereof.

EXAMPLES

Preparation and Characterization of Coatings Comprising Shaped, Dissolvable Polyethylene Glycol (PEG) Tips. The examples use punctal plugs for purposes of demonstration. As is evident, these examples are applicable to prostheses in general. Furthermore, the punctal plugs exemplified below can be employed as drug delivery depots, for delivery of drug to the tear fluid from its position in the canaliculus. In addition, depots bearing dissolvable tips can be used to deliver drug to other lumens into which they are inserted or implanted.

1: Examples of Forming of PEG Tip by Dipping into Molten PEG

Multiple experiments were performed using this process. Temperature and Molecular Weight were both varied, and output characteristics such as shape and size were documented. Molecular weight refers to a weight average molecular weight unless otherwise specified.

1.1: 3.35 k PEG Melt

Ten (10) punctum plugs that were previously gamma irradiated, and having a mean diameter of 0.69 mm (range 0.67 mm-0.70 mm), were obtained, and one end of each plug was dipped twice in rapid succession into the violet 3.35 kDa (3,350 dalton) PEG melt (containing D&C Violet #2), forming a coating in the shape of a rounded dome on the tip of each plug. The resulting dome, also referred to as a PEG tip when made of PEG and placed on an end of a prosthesis, had a mean diameter of 0.72 mm (range of 0.69 mm-0.82 mm), and extended from the end of the punctum plug by a mean length of 0.35 mm (range of 0.34 mm-0.37 mm). In a nitrogen-purged glove box, each sample was placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. Foam holders were then sealed in individual foil pouches. The samples were then gamma irradiated at a dose of 25-35 kGy.

Twelve (12) additional punctum plugs that were not previously irradiated were also obtained. Six (6) of these, having a mean diameter of 0.69 mm (range of 0.67 mm-0.72 mm), were dipped a single time into the same 3.35 k PEG melt, forming a rounded dome on the tip of each plug. The resulting dome had a mean diameter of 0.70 mm (range of 0.66 mm-0.73 mm), and extended from the end of the punctum plug by a mean length of 0.25 mm (range of 0.22 mm-0.29 mm). In a Nitrogen-purged glove box, each sample was placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. Foam holders were then sealed in individual foil pouches. The samples were then gamma irradiated at a dose of 25-35 kGy. Following irradiation, one sample was placed in 37° C. PBS solution under a microscope and the time for the tip to completely dissolve was observed. The tip completely dissolved within 150 sec.

The remaining six (6), having a mean diameter of 0.69 mm (range of 0.67 mm-0.70 mm), were dipped twice in rapid succession into the same 3.35 k PEG melt (same process as that used for the previously irradiated samples), forming a rounded dome on the tip of each plug. The resulting dome had a mean diameter of 0.72 mm (range of 0.68 mm-0.75 mm), and extended from the end of the punctum plug by a mean length of 0.37 mm (range of 0.33 mm-0.41 mm). In a nitrogen-purged glove box, each sample was placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. Foam holders were then sealed in individual foil pouches. The samples were then gamma irradiated at a dose of 25-35 kGy. Following irradiation, one sample was placed in 37° C. PBS solution under a microscope and the time for the tip to completely dissolve was observed. The tip completely dissolved within 135 sec.

It was observed that the number of dips controlled dimensions of the resulting PEG tip, so that the coating thickness was readily controllable. A higher molecular weight PEG resulted in a larger PEG tip relative to use of a lower molecular weight PEG. A previous irradiation of the plug did not appear to impact PEG tip application. And a time of a PEG tip dissolution time was primarily controlled by the molecular weight of the PEG tip material, when coatings of comparable dimensions were compared. Taken together, these observations indicate that the coatings can be well controlled in regards to the final shape, volume, and dimensions of the coating.

1.2: 8 k PEG Melt

An aluminum weigh boat was placed on a hot plate and the bottom coated with a layer of 8 kDa molecular weight PEG powder (8 k PEG). The hot plate was set to 85° C. to melt the PEG. Once molten, a trace amount of D&C Violet #2 was added and mixed into the melt. Ten (10) dried hydrogel punctum plugs were obtained, having an average diameter of 0.71 mm. One end of each plug was dipped twice in rapid succession into the violet 8k PEG melt, forming a rounded dome on the tip of each plug. The resulting PEG tips were measured to have a mean diameter of 0.82 mm (range of 0.73 mm-0.97 mm), and extended from the end of the punctum plug by a mean length of 0.46 mm (range of 0.36 mm-0.55 mm). In a nitrogen-purged glove box, each sample was placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. Foam holders were then sealed in individual foil pouches. The samples were then gamma irradiated at a dose of 25-35 kGy. Following irradiation, two samples were placed in 37° C. PBS solution under a microscope and the time for the tip on each sample to completely dissolve was observed. The tip completely dissolved within 225 sec for each sample.

TABLE 1

Initial 8k PEG vs 3.35k PEG Tip Characterization

| PEG MW (kDa) | # of Dips into PEG Melt | Average Values Measured | | PEG Tip Length (mm) | Time to Dissolve (sec) |
|---|---|---|---|---|---|
| | | Plug Starting ø (mm) | PEG Tip ø (mm) | | |
| 8 | 2 | 0.71 | 0.82 | 0.46 | 225 |
| 3.35 | 1 | 0.69 | 0.70 | 0.25 | 150 |
| 3.35 | 2 | 0.69 | 0.72 | 0.37 | 135 |

2: Examples of 8 k PEG Melt Temperature Determination

An aluminum weigh boat was placed on a hot plate and the bottom coated with a layer of 8 kDa molecular weight PEG powder (8 k PEG). The hot plate was set to 85° C. to melt the PEG. Once molten, a trace amount of D&C Violet #2 was added and mixed into the melt. Upon homogeneity of the mixture, the PEG/dye mixture was transferred to a hot plate set to 70° C. Twelve (12) plugs with a mean diameter of 0.70 mm (range 0.68 mm-0.73 mm), were obtained, and one end of each plug was dipped was dipped twice, in rapid succession, into the violet 8k PEG melt, forming a rounded dome on the tip of each plug. The resulting dome had a mean diameter of 0.70 mm (range of 0.68 mm-0.73 mm), and extended from the end of the punctum plug by a mean length of 0.27 mm (range of 0.21 mm-0.34 mm).

An aluminum weigh boat was placed on a hot plate and the bottom coated with a layer of 8 kDa molecular weight PEG powder (8 k PEG). The hot plate was set to 85° C. to melt the PEG. Once molten, a trace amount of D&C Violet #2 was added and mixed into the melt. Upon homogeneity of the mixture, the PEG/dye mixture was transferred to a hot plate set to 55° C. Twelve (12) plugs with a mean diameter of 0.69 mm (range 0.66 mm-0.71 mm), were obtained, and one end of each plug was dipped twice, in rapid succession, into the violet 8 k PEG melt, forming a rounded dome on the tip of each plug. The resulting dome had a mean diameter of 0.70 mm (range of 0.67 mm-0.72 mm), and extended from the end of the punctum plug by a mean length of 0.36 mm (range of 0.28 mm-0.48 mm).

An aluminum weigh boat was placed on a hot plate and the bottom coated with a layer of blue 8 k PEG. The blue 8 k PEG consisted of 5 g 8 k PEG, 10 mL WFI, and 0.2 mg FD&C Blue #1 that was previously melted, then aliquoted into vials and lyophilized to dry. The hot plate was set to 80° C. to melt the blue 8 k PEG. Upon homogeneity of the mixture, the PEG/dye mixture was transferred to a hot plate set to 62° C. Ten (10) plugs were obtained, and one end of each plug was dipped was dipped twice, in rapid succession, into the blue 8 k PEG melt, forming a rounded dome on the tip of each plug. The resulting dome had a mean diameter of 0.70 mm (range of 0.66 mm-0.75 mm), and extended from the end of the punctum plug by a mean length of 0.32 mm (range of 0.29 mm-0.36 mm).

An aluminum weigh boat was placed on a hot plate and the bottom coated with a layer of blue 8 k PEG. The hot plate was set to 80° C. to melt the PEG. Upon homogeneity of the mixture, the PEG/dye mixture was transferred to a hot plate set to 58° C. Eighteen (18) plugs with a mean diameter of 0.71 mm (range 0.68 mm-0.73 mm) were obtained, and one end of each plug was dipped was dipped twice, in rapid succession, into the blue 8 k PEG melt, forming a rounded dome on the tip of each plug. The resulting dome had a mean diameter of 0.73 mm (range of 0.67 mm-0.80 mm), and extended from the end of the punctum plug by a mean length of 0.33 mm (range of 0.25 mm-0.41 mm).

TABLE 2

PEG Melt Temperature Impact on PEG Tip Dimensions

| Temperature (° C.) | Avg. Plug Starting Diameter (mm) | Avg. PEG Tip Diameter (mm) | Avg. PEG Tip Length (mm) |
|---|---|---|---|
| 55 | 0.69 | 0.70 | 0.36 |
| 58 | 0.71 | 0.73 | 0.33 |
| 62 | N/R | 0.70 | 0.32 |
| 70 | 0.70 | 0.70 | 0.27 |

Observations:
At 55° C., PEG melt began to solidify after 10 min.
PEG Tip length decreases as melt temperature increases.
62° C. was selected because there was lower risk of the PEG solidifying since it was maintained in a melted state. The lowest temperature that would keep the PEG melted was advantageous since it reduced the risk of lowering the PEG viscosity and creating shorter tips.

3: Examples of Effect of PEG Tip on Hydration of Punctum Plug

One (1) punctum plug with PEG tip was obtained. One end of the punctum plug was dipped twice in rapid succession into the 8k PEG/Blue Dye #1 melt on a 62° C. hot plate, prepared using the same methods as described in Example 2. Samples were placed in 37° C. PBS solution under a microscope and images were saved every 3 s recording the dissolution of the PEG tip over time. See FIG. 7.

Swelling of No PEG Tip vs. Double Dip PEG Tip at t≈0, 30 s, and 60 s

One (1) punctum plug was obtained. One end of the punctum plug was dipped twice in rapid succession into the 8 k PEG/FD&C Blue #1 melt on a 62° C. hot plate, prepared using the same methods as described in Example 2. The other end of the plug was dipped a single time into the same blue 8k PEG melt, forming a rounded dome on the tip of the plug. The sample was placed in 37° C. PBS solution under a microscope and an image was saved every 3 seconds recording the dissolution of the PEG tip and PEG coating over time. See FIG. 8, which is an image of the swelling of punctum plug with the PEG tip and PEG coat at t=30 s.

Three (3) punctum plugs were obtained. One end of each punctum plug was dipped twice in rapid succession into the 8 k PEG/FD&C Blue #1 melt, prepared using the same methods as Example 2. The other end of one (1) plug was dipped two times in rapid succession into the same blue 8 k PEG melt, forming a rounded dome on the tip of the plug. The other end of a second plug was dipped a single time into the same blue 8 k PEG melt, and then depressed against a weight boat, forming a smaller, flat PEG tip. The other end of the third sample was not PEG tipped. All three (3) samples were placed in 37° C. PBS solution under a microscope and an image was saved every 3 s recording the dissolution of each PEG tip and PEG coating over time. See FIG. 9, which is an image of swelling of a non-coated prosthesis as compared to a single dip and double dip PEG coat, with t=30, 45, 60 s.

TABLE 3

Hydration Rate of Plug End with no PEG Coating vs

| Type of PEG Coating | t = 30 s | t = 45 s | t = 60 s |
|---|---|---|---|
| None | 0.64 mm | 0.67 mm | 0.69 mm |
| Depressed Single | 0.53 mm | 0.57 mm | 0.62 mm |
| Double Dip | 0.51 mm | 0.53 mm | 0.55 mm |

Observations:
Coating delays the start of plug hydration.
Coating decreases the hydration rate of the punctum plug end featuring the coating.
The amount of PEG material on the end of the punctum plug affects the coating dissolution rate. The greater the amount of PEG, the slower the PEG tip dissolution rate.

4: Examples of PEG Tip Dimensions vs Number of Dips Into the PEG Melt

An aluminum weigh boat was placed on a hot plate and the bottom coated with a layer of 3.35 kDa molecular weight PEG powder (3.35 k PEG). The hot plate was set to 85° C. to melt the PEG. Once molten, a trace amount of D&C Violet #2 was added and mixed into the melt. Eighteen (18) punctum plugs with a mean diameter of 0.73 mm (range 0.69 mm-0.78 mm), were obtained, and one end of each plug was dipped once into the violet 3.35 k PEG melt, forming a rounded dome on the tip of each plug. The resulting dome had a mean diameter of 0.75 mm (range of 0.69 mm-0.84 mm), and extended from the end of the punctum plug by a mean length of 0.24 mm (range of 0.19 mm-0.32 mm).

Twenty-two (22) punctum plugs with a mean diameter of 0.71 mm (range 0.66 mm-0.74 mm), were obtained, and one end of each plug was dipped twice, in rapid succession into the violet 3.35 k PEG melt, forming a rounded dome on the tip of each plug. The resulting dome had a mean diameter of 0.73 mm (range of 0.69 mm-0.88 mm), and extended from the end of the punctum plug by a mean length of 0.28 mm (range of 0.22 mm-0.43 mm). Eighteen (19) punctum plugs with a mean diameter of 0.74 mm (range 0.70 mm-0.77 mm), were obtained, and one end of each plug was dipped once into the violet 3.35 k PEG melt, forming a rounded dome on the tip of each plug. The resulting dome had a mean diameter of 0.75 mm (range of 0.67 mm-0.80 mm), and extended from the end of the punctum plug by a mean length of 0.27 mm (range of 0.22 mm-0.34 mm).

Eighteen (18) punctum plugs with a mean diameter of 0.71 mm (range 0.68 mm-0.75 mm), were obtained, and one end of each plug was dipped twice, in rapid succession into the violet 3.35 k PEG melt, forming a rounded dome on the tip of each plug. The resulting dome had a mean diameter of 0.72 mm (range of 0.67 mm-0.78 mm), and extended from the end of the punctum plug by a mean length of 0.34 mm (range of 0.25 mm-0.45 mm).

TABLE 4

PEG Tip Length vs PEG Molecular Weight and Number of Dips into the PEG Melt

| PEG Molecular Weight (kDa) | # of Dips into PEG Melt | Avg. Plug Starting Diameter (mm) | Avg. PEG Tip Diameter | Avg. PEG Tip Length |
|---|---|---|---|---|
| 3.35 | 1 | 0.73 | 0.75 | 0.24 |
| 3.35 | 2 | 0.71 | 0.73 | 0.28 |
| 8 | 1 | 0.74 | 0.75 | 0.27 |
| 8 | 2 | 0.71 | 0.72 | 0.34 |

Observations:
PEG tip length increased with higher molecular weight PEG
PEG tip length can be controlled by the number of dips into the PEG melt 5: Examples of Effects of Gamma Irradiation 5.1: Dissolution of 8 k PEG/FD&C Blue #1 Tip Post-Gamma at 25-35 kGy Three (3) punctum plugs having a mean diameter of 0.66 mm (range 0.65 mm-0.67 mm) were obtained, and one end of each plug was dipped twice in rapid succession into the blue 8 k PEG melt, forming a rounded dome on the tip of each plug. The resulting dome extended from the end of the punctum plug by a mean length of 0.41 mm (range of 0.31 mm-0.47 mm). In a Nitrogen-purged glove box, each sample was placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. Foam holders were then sealed in individual foil pouches. The samples were then gamma irradiated at a dose of 25-35 kGy. Three (3) 15 mL conical tubes were filled with pH 7.4 Phosphate Buffer Saline (PBS) solution. The tubes were placed in a 37° C. water bath allowing the PBS to equilibrate. Each plug was placed in a tube to hydrate the plug and dissolve the PEG Tip. After five (5) minutes, the plugs were removed from the PBS and the presence of PEG Tip was evaluated under a Unitron microscope. There was no PEG Tip presence after five (5) minutes in solution.

Three (3) gamma irradiated (25-35 kGy) double PEG tipped punctum plugs were obtained and placed in 37° C. PBS solution under a microscope. The time for the tip on each sample to completely dissolve was observed. The PEG tip length on each sample varied from 0.40 mm to 0.46 mm. The tip completely dissolved within 230 sec for each sample.

5.2: Dissolution of 8 kDa PEG/FD&C Blue #1 Tip Post-Gamma at 18.5-22.5 kGy

An aluminum weigh boat was preheated on a hot plate set to 70° C. One vial of lyophilized 8 k PEG/FD&C blue #1 mixture was added to the preheated aluminum weigh boat. Before PEG tipping plugs, the hot plate temperature was decreased to 58° C. Five (5) punctum plugs with a mean diameter of 0.64 mm (range 0.59 mm to 0.68 mm) were obtained and one end of the plug was dipped twice, in rapid succession, into the blue 8 k PEG melt, forming a rounded dome on the tip of the plug. The resulting dome had a mean diameter of 0.68 mm (range of 0.65 mm-0.72 mm), and extended from the end of the punctum plug by a mean length of 0.38 mm (range of 0.28 mm-0.49 mm). Each sample was placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. In a Nitrogen-purged glove box, foam holders were sealed in individual foil pouches. The samples were then gamma irradiated at a dose of 18.5-22.5 kGy. Following irradiation, each sample was placed in 37° C. PBS solution under a microscope and the time for the tip on each sample to completely dissolve was observed. The tip completely dissolved within 300 sec for each sample.

Observations:
Irradiated PEG tip materials dissolve rapidly and irradiation does not significantly impact dissolution rate.
In these examples, all PEG tips dissolved in less than five minutes.

6: Examples of Impact of Time on PEG Melt Characteristics and Resulting PEG Tips An aluminum weigh boat was preheated on a hot plate set to 80° C. One vial of lyophilized 8 k PEG/FD&C blue #1 mixture was added to the preheated aluminum weigh boat. The blue 8 k PEG consisted of 5 g 8 k PEG, 10 mL WFI, and 0.2 mg FD&C Blue #1 that was previously melted, then aliquoted into vials and lyophilized to dry. Once fully melted, the aluminum weight boat containing the PEG melt was transferred to a second hot plate set to 62° C. Thirty-five (35) punctum plugs were obtained and one end of the plug was dipped twice, in rapid succession, into the blue 8 k PEG melt, forming a rounded dome on the tip of the plug at each time point. Time points consisted of 5, 15, 60, 120, and 150 minutes.

The resulting PEG tips created at the five (5) minute time point were measured to have a mean diameter of 0.71 mm (range of 0.69 mm-0.75 mm), and extended from the end of the punctum plug by a mean length of 0.32 mm (range of 0.31 mm-0.33 mm). The resulting PEG tips created at the fifteen (15) minute time point were measured to have a mean diameter of 0.69 mm (range of 0.66 mm-0.72 mm), and extended from the end of the punctum plug by a mean length of 0.32 mm (range of 0.29 mm-0.36 mm). The resulting PEG tips created at the sixty (60) minute time point were measured to have a mean diameter of 0.69 mm (range of 0.67 mm-0.71 mm), and extended from the end of the punctum plug by a mean length of 0.32 mm (range of 0.30 mm-0.34 mm). The resulting PEG tips created at the 120 minute time point were measured to have a mean diameter of 0.73 mm (range of 0.68 mm-0.78 mm), and extended from the end of the punctum plug by a mean length of 0.40 mm (range of 0.32 mm-0.45 mm). The resulting PEG tips created at the 150 minute time point were measured to have a mean diameter of 0.73 mm (range of 0.69 mm-0.73 mm), and extended from the end of the punctum plug by a mean length of 0.42 mm (range of 0.32 mm-0.48 mm).

TABLE 5

Impact of Duration of PEG Melt Time at 62° C. on PEG Tip Length

| Timepoint (min) | Avg. PEG Tip Diameter (mm) | Avg. PEG Tip Length (mm) |
| --- | --- | --- |
| 5 | 0.71 | 0.32 |
| 15 | 0.69 | 0.32 |
| 60 | 0.69 | 0.32 |
| 120 | 0.73 | 0.40 |
| 150 | 0.73 | 0.42 |

An aluminum weigh boat was preheated on a hot plate set to 58° C. One vial of the same lyophilized 8 k PEG/FD&C blue dye #1 mixture was added to the preheated aluminum weigh boat. The temperature of the hot plate was increased to 65° C. to fully melt the 8 k PEG/dye mixture. Before PEG Tipping plugs, the hot plate temperature was decreased to 58° C. Ten (10) punctum plugs with a mean diameter of 0.71 mm (range 0.67 mm to 0.75 mm) were obtained and one end of the plug was dipped twice, in rapid succession, into the blue 8 k PEG melt, forming a rounded dome on the tip of the plug at each time point. Time points consisted of 0, 15, 30, 60, 120, and 150 minutes.

TABLE 6

Impact of Duration of PEG Melt
Time at 58° C. on PEG Tip Length

| Timepoint (min) | Avg. Plug Starting Diameter (mm) | Avg. PEG Tip Diameter (mm) | Avg. PEG Tip Length (mm) |
|---|---|---|---|
| 0 | 0.71 | 0.73 | 0.30 |
| 15 | 0.71 | 0.72 | 0.28 |
| 30 | 0.70 | 0.71 | 0.27 |
| 60 | 0.71 | 0.74 | 0.26 |
| 90 | 0.70 | 0.72 | 0.27 |
| 120 | 0.71 | 0.72 | 0.25 |
| 150 | 0.71 | 0.73 | 0.28 |

An aluminum weigh boat was preheated on a hot plate set to 80° C. One vial of lyophilized 8 k PEG/FD&C blue #1 mixture was added to the preheated aluminum weigh boat. Once fully melted, the aluminum weight boat containing the PEG melt was transferred to a second hot plate set to 58° C. Ten (10) punctum plugs with a mean diameter of 0.70 mm (range 0.65 mm to 0.74 mm) were obtained and one end of the plug was dipped twice, in rapid succession, into the blue 8 k PEG melt, forming a rounded dome on the tip of the plug at each time point. Time points consisted of 120, 135, 185, 225, and 255 minutes.

TABLE 7

Evaluation of Longer PEG Melt Hold Duration at 58° C.

| Timepoint (min) | Avg. Plug Starting Diameter (mm) | Avg. PEG Tip Diameter (mm) | Avg. PEG Tip Length (mm) |
|---|---|---|---|
| 120 | 0.69 | 0.71 | 0.30 |
| 135 | 0.71 | 0.71 | 0.38 |
| 185 | 0.68 | 0.74 | 0.51 |
| 225 | 0.70 | 0.73 | 0.35 |
| 255 | 0.69 | 0.71 | 0.35 |

An aluminum weigh boat was preheated on a hot plate set to 80° C. One vial of lyophilized 8 k PEG/FD&C blue #1 mixture was added to the preheated aluminum weigh boat. Once fully melted, the aluminum weight boat containing the PEG melt was transferred to a second hot plate set to 58° C. Ten (10) punctum plugs with a mean diameter of 0.69 mm (range 0.65 mm to 0.73 mm) were obtained and one end of the plug was dipped twice, in rapid succession, into the blue 8 k PEG melt, forming a rounded dome on the tip of the plug at each time point. Time points consisted of 0, 30, 60, and 90 minutes.

TABLE 8

Impact of Duration of PEG Melt
Time at 62° C. on PEG Tip Length

| Timepoint (min) | Avg. Plug Starting Diameter (mm) | Avg. PEG Tip Diameter (mm) | Avg. PEG Tip Length (mm) |
|---|---|---|---|
| 0 | 0.71 | 0.72 | 0.34 |
| 30 | 0.70 | 0.74 | 0.32 |
| 60 | 0.68 | 0.74 | 0.33 |
| 90 | 0.68 | 0.72 | 0.37 |

Observations:
In order to obtain a homogeneous PEG melt, hot plate temperature for this mixture of polymers needs to be set higher than 58° C.
After 120 minutes, the PEG melt became shallow resulting in shorter PEG Tips. PEG reservoir depth must be kept sufficiently high for full tip formation.
During these evaluations, the PEG melt was occasionally transferred back to the higher temperature (80° C.) hot plate if the melt began to solidify. It was then able to be transferred back to the lower temperature plate without noticeable impact on PEG Tip formation.
The stability window for PEG melt Tipping at 58° C. and 62° C. are the same.
The color of the 8 k PEG/FD&C blue dye #1 melt was observed for the duration of the study. At the time of the initial melt, the PEG melt was royal blue. At 150 minutes, the melt color was dark teal. There was no observable color difference between the PEG Tips produced at these different time points.

7: Example of Formation of PEG Tip by Applying in a Thin Walled Tube, then Shaping Via Heated Plate:

Linear PEG having a molecular weight of 35 kDa (35 k PEG) was added to an aluminum weigh boat, covering the bottom of the entire weigh boat. The weigh boat was then placed on a hot plate set to 90° C. to melt. While melting the PEG, twenty (20) dried hydrogel punctum plugs having a diameter 0.7 mm to 0.75 mm were loaded into polyimide tubing having an inner diameter of approximately 0.76 mm and recessed approximately 0.7 mm to 1 mm from the opening of the tube. The end of each tube from which the dried rod was recessed was then dipped repeatedly into the melt to allow the molten PEG to wick into the space between the tip of the dried rod and the end of the tube. Excess PEG was wiped off of the outside of the polyimide and the PEG was wiped flush with the end of the tube on a warm metal plate placed on the hot plate. Each sample was then set aside to cool.

Once cooled, samples were pushed from the opposite end of the dried hydrogel rod using a length of steel wire, until the now-hardened PEG tip was protruding from the polyimide tube. Each PEG tip was held at an angle of approximately 40 held at an angle of approximately 30° to 45° to the warm metal plate, then rotated quickly across the surface while maintaining this angle to taper the PEG tip. Each sample was then removed from the polyimide tubes using the wire. PEG tips remained adhered to the end of the dried hydrogel rods, and some PEG was observed to have wicked around the sides of the dried rods while inside the tubing.

Five (5) samples were measured to determine the approximate dimensions of the PEG tip. The length of each PEG tip was found to be between 0.59 mm-0.73 mm from the end of the hydrogel, and the diameter of each was 0.76 mm-0.78 mm. Samples were then placed into a custom foam holder consisting of a 0.063" (1.6 mm) thick piece of closed cell urethane foam with a hole punched through the 0.063" edge to accept the hydrogel rod with PEG tip, each with the PEG tip end inserted into the foam. The foam holders containing the samples were sealed in individual foil pouches and shaken and dropped. Samples were then removed from the foil and foam and observed. PEG tips remained adhered to each sample and showed no signs of damage.

8: Examples of Color Addition to PEG Tip Materials

Color may be added to the PEG material to provide visual contrast. PEG Tips were applied to dried hydrogel rods that were yellow to off-white in color, therefore darker contrasting colors were added to the PEG Tip material.

Linear PEG having a molecular weight of 35 kDa (35 k PEG) was added to an aluminum weigh boat, covering the bottom of the entire weigh boat. The weigh boat was then placed on a hot plate set to 90° C. to melt. A pinch of FD&C Blue #1 was added to the molten PEG and stirred in with a metal spatula. Resulting material was observed to be greenish in hue with particles of the FD&C Blue #1 visibly dispersed throughout, both when molten and after the material was removed from the heat source and allowed to cool and harden, indicating that FD # C Blue #1 is not readily soluble in the 35 k PEG.

In a separate aluminum weigh boat, a pinch of FD&C Blue #1 was dissolved in water for injection (WFI). The weigh boat was then moved to the 90° C. hot plate and allowed to equilibrate. A small amount of 35 k PEG was then added to the warm solution a few flakes at a time until the weigh boat appeared to be approximately 50% full. The hot plate was then turned down to 80° C. and the PEG/FD&C Blue #1/WFI solution was left on the hot plate overnight to evaporate. The resulting PEG melt was blue in color and no FD&C Blue #1 flakes were visible. PEG tips were then made with this material using the methods to form, shape, and package the samples described in Example 7. Dried hydrogel rods and Polyimide tubing used were smaller in diameter, with the hydrogel rods ≤0.65 mm and the polyimide tube inner diameter approximately 0.65 mm.

Lissamine Green B was added to molten 35k PEG via a similar method. A solution of 0.1% Lissamine Green B in WFI was mixed and 27.7 g of the resulting solution was heated on a 90° C. hot plate. A total of 28.8 g of 35 k PEG was added to the solution in the same controlled fashion and allowed to dry overnight on the hot plate set at 80° C. Resulting material was approximately 0.09% Lissamine Green B in 35 k PEG, and appeared a very deep green with no particles of Lissamine Green B visible. PEG tips were then made with this material using the methods to form, shape, and package the samples described in Example 7. Dried hydrogel rods and Polyimide tubing used were smaller in diameter, with the hydrogel rods ≤0.65 mm and the polyimide tube inner diameter approximately 0.65 mm.

Other colorants, such as FD&C Violet #2, are known to be readily soluble in molten PEG and may be added without first dissolving in water.

9: Example of Forming of PEG Tip by Molding

PEG tips were applied to one end of a dried hydrogel rod using a 2-plate mold. The bottom half of the mold consisted of an array hemispherical depressions having a diameter of 0.76 mm. The top plate of the mold consisted of an array of 0.78 mm diameter through holes that, when the top half was properly placed onto the bottom half of the mold, aligned with the depressions in the bottom half.

The bottom half of the mold was placed onto the hot plate set at 100° C. In an aluminum weigh pan, 35k PEG was melted on same hot plate. A small amount of D&C Violet #2 was added to the melt and stirred in with a metal spatula to aid visualization. The melt was then applied to a section of the hot bottom plate of the mold, with a mold surface temperature of ≥75° C. A stainless steel blade was used to drag the melt across the surface of the mold to fill the depressions while leaving minimal material outside of the depressions on the plate. Excess material was removed using the blade. The bottom plate was removed from the heat source and the top plate aligned and positioned on top of it. Four (4) 0.65 mm diameter hydrogel rods inside polyimide tubing were slid into four of the through holes in the top half of the mold that aligned with the section of the bottom plate containing the PEG melt. The rods were depressed into the melt using a length of steel wire. The top surface temperature of the mold was measured to be 41° C. at this time. The mold was allowed to cool at room temperature until the top surface temperature was measured to be 28° C. Plates were separated and samples removed. Three (3) samples retained hemispherical shaped PEG tips, with some flash formed along the parting line of the mold plates.

Molding process was repeated as described above, this time using two molds having the same design and dimensions. The molds were clamped together before inserting dried hydrogel rods, and following placement of the rods the molds were transferred into a −40° C. freezer to accelerate cooling, with a total cooling time of approximately 20 minutes. Molds were then removed from the freezer and plates were separated and samples removed. All six samples made retained hemispherical shaped PEG tips, and one sample included some flash formed along the parting line of the mold plates.

Further Disclosure

All patents, patent applications, journal articles, and publications referenced herein are hereby incorporated herein by reference for all purposes; in case of conflict, the instance specification is controlling.

1A. A prosthesis for a lacrimal canaliculus comprising a swellable punctal plug with a proximal end and a distal end, with the plug comprising a water-dissolvable biocompatible coating on the distal and/or the proximal end.

1B. A prosthesis for placement in a lumen, the prosthesis comprising a water-dissolvable biocompatible coating on the distal and/or the proximal end.

1C. A prosthesis for placement in or across natural or prosthetic lumens, ostia, ducts, sinus, or sphincters, the prosthesis comprising a coating. The prosthesis may include a distal end for insertion into the same.

1D. A prosthesis for passage into an opening in a tissue, the prosthesis comprising a coating.

1E. A prosthesis for passage into an opening in a tissue, the prosthesis comprising a coating, the prosthesis sized to place the coating in contact with the tissue around the opening.

2. The prosthesis of 1 (referring to 1A, 1B . . . 1n) wherein the coating comprises a water-soluble material, a hydrophilic material, or a hydrophobic material.

3. The prosthesis of 1 wherein the coating consists essentially of a water soluble material or consists essentially of a hydrophobic material, or consists essentially of a hydrophilic material.

4. The prosthesis of any of 1-3 wherein the material comprises a hydrophilic polymer.

5. The prosthesis of any of 1-4 wherein the water soluble material comprises a hydrophilic polymer that comprises polyethylene glycol, polyvinyl alcohol, polyvinylpyrrolidone, cellulose, polyacrylic acid, polyethyleneimine, peptide, or polysaccharide.

6. The prosthesis of any of 1-5 wherein the material is a solid at a physiological temperature and has a melting point in a range from 40 to 100° C.

7. The prosthesis of any of 1-6 wherein the coating essentially dissolves in a physiological solution in no more than 15 minutes. Or no more than any of: 0.5, 1, 2, 3, 4, 5, 10, 15 minutes.

8. The prosthesis of any of 1-7 wherein the coating covers the proximal end and does not contact the distal end.

9. The prosthesis of any of 1-7 wherein the coating covers the distal end and does not contact the proximal end.

10. The prosthesis of 8 or 9 wherein a surface area that extends from the proximal end to the distal end is substantially free of the coating. One or both of the proximal end and the distal end may comprise the coating.

11. The prosthesis of 8 or 9 wherein a surface area that extends from the proximal end and the distal end is covered by the coating.

12. The prosthesis of any of 1-7 wherein the coating encapsulates the prosthesis e.g., a punctal plug.

13. The prosthesis of any of 1-12 wherein the coating is not crosslinked.
14. The prosthesis of any of 1-13 wherein the coating is free of functional groups that form covalent bonds (free of functional groups that form covalent bonds when the coating contacts a solution, e.g., an aqueous solution).
15. The prosthesis of any of 1-14 wherein the coating has a thickness from 1 to 5000 microns. Artisans will immediately appreciate that all ranges and values between the explicitly stated bounds are contemplated, with any of the following being available as an upper or lower limit: 1, 2, 3, 4, 5, 10, 20, 25, 50, 100, 1000, 2000 microns.
16. The prosthesis of any of 1-15 with the coating further comprising a visualization agent detectable by an unaided human eye.
17. The prosthesis of any of 1-15 with the coating further comprising a visualization agent detectable by a unaided human eye, wherein the agent is disposed at the distal end but not the proximal end, the agent is disposed at the proximal end but not the distal end, or the agent is disposed at the distal end and the proximal end.
18. The prosthesis of any of 1-17 with the proximal end and/or the distal end being tapered.
19. The prosthesis of 18 wherein the coating provides the taper.
20. The prosthesis of 18 wherein the prosthesis e.g., a plug provides the taper, with the coating overlaying the taper while preserving a tapered profile.
21. The prosthesis of any of 19-20 with the distal end comprising the coating and the visualization agent, with the proximal end being free of: the visualization agent and/or the coating.
22. The prosthesis of any of 1-21 wherein the prosthesis e.g., a plug, when placed in physiological solution and allowed to freely expand, swells from 10% to 300% in volume.
23. The prosthesis of any of 1-21 wherein the prosthesis e.g., a plug further comprises a therapeutic agent.
24. The prosthesis of any of 1-23 wherein the prosthesis e.g., a plug, without the coating, swells preferentially at an end relative to a central portion.
25. The prosthesis of any of 1-24 wherein the prosthesis e.g., a plug is made of essentially one material.
26. The prosthesis of 25 wherein the material comprises a plurality of polymers.
27. A method of applying a coating to a prosthesis, e.g., a punctal plug, comprising melting a polymer and dipping the prosthesis into the melt, with the polymer being a solid at 37° C. Alternatively: spraying, adsorbing, or brushing the polymer onto the prosthesis instead of dipping.
28. A method of applying a coating to a prosthesis, e.g., a punctal plug, comprising exposing a prosthesis to a solution comprising the polymer, with the polymer being in solution in a solvent that is not a solvent for the prosthesis.
28. The method of 28 wherein the solvent is an organic solvent.
29. The prosthesis or method of any of 1-28 wherein the prosthesis is sized and/or for the purpose of, placement in a natural lumen.
30. The prosthesis or method of 29 wherein the lumen is a lumen as set forth herein.
31. A prosthesis for placement in a lumen, the prosthesis comprising a coating on a portion of the prosthesis, wherein the coating comprises a visualization agent to indicate an orientation of the prosthesis at its site of intended use.
32. A use of the prosthesis of any of 1-31 according to a method of any of 27-31. A use of a prosthesis according to any of 1-31 for placement in a lumen. A use of a prosthesis for any of 1-31 for treatment of a medical condition and/or for delivery of a therapeutic agent.
33. The prosthesis, method, or use of any of 1-32 wherein the lumen is a natural lumen or an artificial lumen.
34. The prosthesis, method, or use of any of 1-32 wherein the lumen is one set forth in the Sites of Administration section.
35. A kit comprising a prosthesis of any of 1-31 and/or for a use as any of 32-34.

The invention claimed is:
1. A prosthesis for passage into an opening in a tissue, the prosthesis comprising
a swellable punctal plug with a body having a proximal end and a distal end, wherein the plug, when placed in physiological solution and allowed to freely expand, swells from 10% to 300% in volume,
the prosthesis further comprising a water-dissolvable coating on the swellable punctal plug that forms an ellipsoid shape such that the ellipsoid covers a portion of the body and the distal end and continuously extends from 0.1 mm to 3 mm beyond the distal end to provide a tip for the prosthesis.
2. The prosthesis of claim 1 wherein the coating comprises a water soluble material.
3. The prosthesis of claim 2 wherein the water soluble material consists essentially of a hydrophilic polymer.
4. The prosthesis of claim 2 wherein the water soluble material comprises a hydrophilic polymer that comprises polyethylene glycol, polyvinyl alcohol, polyvinylpyrrolidone, cellulose, polyacrylic acid, polyethyleneimine, peptide, or polysaccharide.
5. The prosthesis of claim 1 wherein the coating encapsulates the punctal plug.
6. The prosthesis of claim 1 wherein the plug and/or coating further comprises a therapeutic agent.
7. The prosthesis of claim 6 wherein the agent is for treatment of an ocular condition.
8. The prosthesis of claim 7 wherein the ocular condition is age-related macular degeneration (AMD) cystoid macular edema (CME), diabetic macular edema (DME), posterior uveitis, diabetic retinopathy, or glaucoma.
9. The prosthesis of claim 8 wherein the agent comprises anti-VEGF, a VEGFR1 inhibitor, a VEGFR2 inhibitor, a VEGFR3 inhibitor, anti-PDGF, anti-PDGF-R, a PDGFRβ inhibitor, an anti-angiogenic agent, sunitinib, E7080, Takeda-6d, tivozanib, regorafenib, sorafenib, pazopanib, axitinib, nintedanib, cediranib, vatalanib, motesanib, a macrolide, sirolimus, everolimus, a tyrosine kinase inhibitor (TKI), imatinib, gefinitib, toceranib, erlotinib, nilotinib, bosutinib neratinib, lapatinib, nepafenac, tacrolimus, moxifloxacin, dexamethasone, travoprost, a steroid, a fluoroquinolone, a prostaglandin analog, a prostamide, or an mTOR receptor inhibitor.
10. The prosthesis of claim 1 wherein the coating further comprises a visualization agent detectable by an unaided human eye.
11. The prosthesis of claim 1 wherein the coating is a solid at a physiological temperature and has a melting point in a range from 40 to 100 degrees Celsius.
12. The prosthesis of claim 1 wherein the coating essentially dissolves in a physiological solution in no more than 15 minutes.
13. The prosthesis of claim 1 wherein the coating does not contact the proximal end.

14. The prosthesis of claim 13 wherein the coating comprises a visualization agent to indicate an orientation of the punctal plug.

15. The prosthesis of claim 1 wherein the tip has a rounded terminus.

\* \* \* \* \*

UNITED STATES PATENT AND TRADEMARK OFFICE
CERTIFICATE OF CORRECTION

PATENT NO. : 10,617,563 B2
APPLICATION NO. : 15/217559
DATED : April 14, 2020
INVENTOR(S) : Jarrett et al.

Page 1 of 1

It is certified that error appears in the above-identified patent and that said Letters Patent is hereby corrected as shown below:

In the Specification

In Column 14, Line 44, delete "gefinitib" and insert -- gefitinib, --, therefor.

In Column 17, Line 58, delete "gefinitib" and insert -- gefitinib, --, therefor.

In the Claims

In Column 30, Claim 9, Line 52, delete "gefinitib," and insert -- gefitinib, --, therefor.

Signed and Sealed this
Fourth Day of August, 2020

Andrei Iancu
*Director of the United States Patent and Trademark Office*